(12) United States Patent
Ichinose

(10) Patent No.: US 11,244,458 B2
(45) Date of Patent: Feb. 8, 2022

(54) IMAGE PROCESSING APPARATUS, IMAGE PROCESSING METHOD, AND PROGRAM

(71) Applicant: FUJIFILM Corporation, Tokyo (JP)

(72) Inventor: Akimichi Ichinose, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 53 days.

(21) Appl. No.: 16/927,977

(22) Filed: Jul. 13, 2020

(65) Prior Publication Data
US 2020/0342606 A1    Oct. 29, 2020

Related U.S. Application Data

(63) Continuation of application No. PCT/JP2018/047852, filed on Dec. 26, 2018.

(30) Foreign Application Priority Data

Jan. 29, 2018 (JP) .............................. JP2018-012780

(51) Int. Cl.
*G06K 9/00* (2006.01)
*G06T 7/11* (2017.01)
(Continued)

(52) U.S. Cl.
CPC .................. *G06T 7/11* (2017.01); *G06N 5/04* (2013.01); *G06N 20/00* (2019.01); *G06T 7/0012* (2013.01);
(Continued)

(58) Field of Classification Search
CPC . G06T 7/11; G06T 7/70; G06T 7/0012; G06T 7/60; G06T 2207/10116;
(Continued)

(56) References Cited

U.S. PATENT DOCUMENTS 5,072,384 A * 12/1991 Doi ........................... G06T 7/66
382/132
10,438,357 B2 * 10/2019 Kim ......................... G06T 7/12
(Continued)

FOREIGN PATENT DOCUMENTS

JP    H04125779    4/1992
JP    2005224460    8/2005
(Continued)

OTHER PUBLICATIONS

"International Search Report (Form PCT/ISA/210) of PCT/JP2018/047852," dated Mar. 19, 2019, with English translation thereof, pp. 1-5.
(Continued)

*Primary Examiner* — Van D Huynh
(74) *Attorney, Agent, or Firm* — JCIPRNET

(57) ABSTRACT

Provided are an image processing apparatus, an image processing method, and a program that can collect high-quality correct answer data used for machine learning with a simple method. The image processing apparatus includes: a first extractor that extracts a measurement target region from a medical image, using a result of learning performed using correct answer data of the measurement target region; a measurement object determination unit that determines a measurement object used to measure the measurement target region; a measurement object correction unit that corrects the measurement object in response to a command from a user; and a measurement target region correction unit that corrects the measurement target region extracted by the first extractor, using a correction result of the measurement object. The first extractor performs learning using the measurement target region corrected by the measurement target region correction unit as correct answer data.

18 Claims, 14 Drawing Sheets

(51) Int. Cl.
*G06T 7/70* (2017.01)
*G16H 30/40* (2018.01)
*G06N 20/00* (2019.01)
*G06N 5/04* (2006.01)
*G06T 7/00* (2017.01)
*G06T 7/60* (2017.01)

(52) U.S. Cl.
CPC ................ *G06T 7/60* (2013.01); *G06T 7/70* (2017.01); *G16H 30/40* (2018.01); *G06T 2207/10116* (2013.01); *G06T 2207/20081* (2013.01); *G06T 2207/20092* (2013.01); *G06T 2207/30048* (2013.01); *G06T 2207/30061* (2013.01); *G06T 2207/30096* (2013.01)

(58) Field of Classification Search
CPC . G06T 2207/20081; G06T 2207/20092; G06T 2207/30048; G06T 2207/30061; G06T 2207/30096; G06T 2207/20084; G16H 30/40; G06N 20/00; G06N 5/04; G06N 3/0454; G06N 3/08; A61B 6/03
USPC .......................................................... 382/128
See application file for complete search history.

(56) References Cited

U.S. PATENT DOCUMENTS

| | | | | |
|---|---|---|---|---|
| 2004/0153128 | A1* | 8/2004 | Suresh | G16H 50/30 607/14 |
| 2006/0122480 | A1* | 6/2006 | Luo | G06T 7/0012 600/407 |
| 2008/0252660 | A1* | 10/2008 | Masumoto | G06T 11/203 345/642 |
| 2017/0083796 | A1* | 3/2017 | Kim | G06K 9/00369 |
| 2019/0057503 | A1* | 2/2019 | Nakamura | G06F 16/90344 |
| 2019/0065995 | A1* | 2/2019 | Takayama | G06N 20/00 |
| 2019/0205668 | A1* | 7/2019 | Noda | G08G 1/166 |

FOREIGN PATENT DOCUMENTS

| | | |
|---|---|---|
| JP | 2007222325 | 9/2007 |
| JP | 2008262253 | 10/2008 |
| JP | 2010233879 | 10/2010 |
| JP | 2010259656 | 11/2010 |
| JP | 2014502176 | 1/2014 |
| JP | 2014050527 | 3/2014 |
| JP | 6246287 | 12/2017 |
| JP | 2019010411 | 1/2019 |
| WO | 2012061452 | 5/2012 |

OTHER PUBLICATIONS

"Written Opinion of the International Searching Authority (Form PCT/ISA/237) of PCT/JP2018/047852," dated Mar. 19, 2019, with English translation thereof, pp. 1-7.

* cited by examiner

FIG. 8
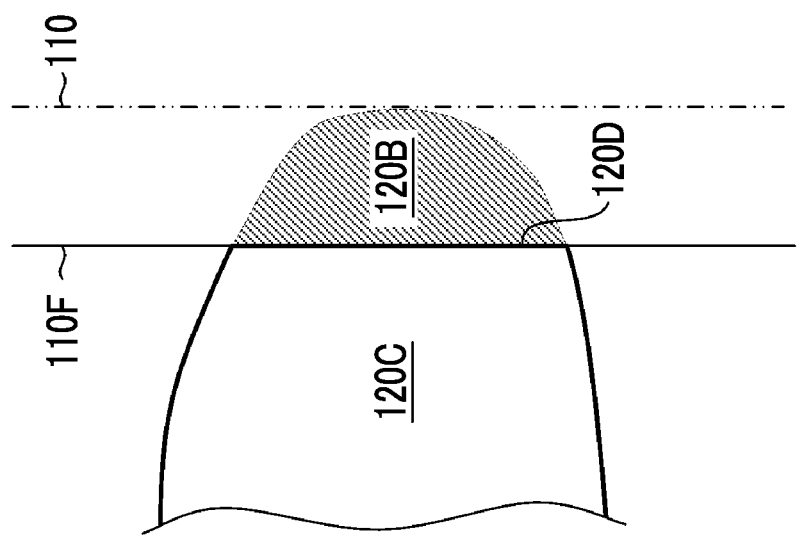
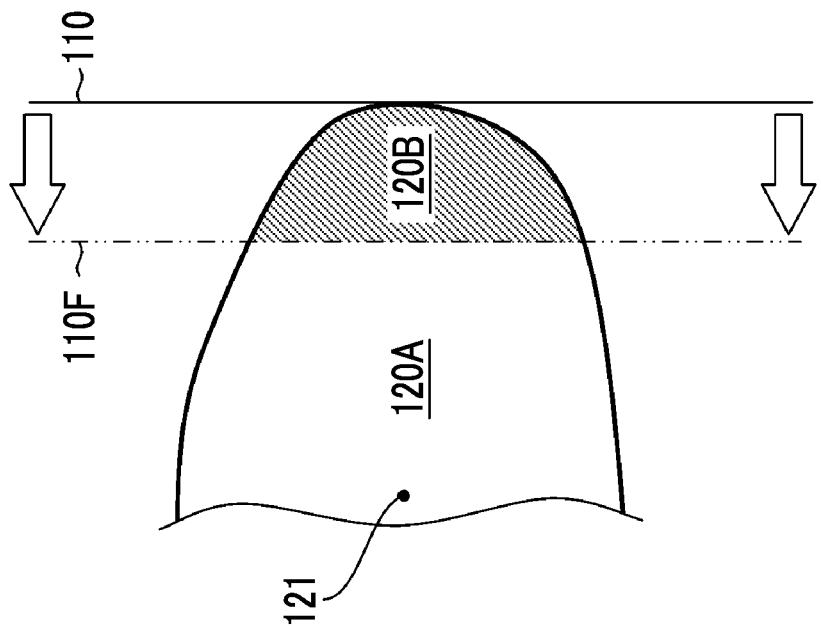

FIG. 9
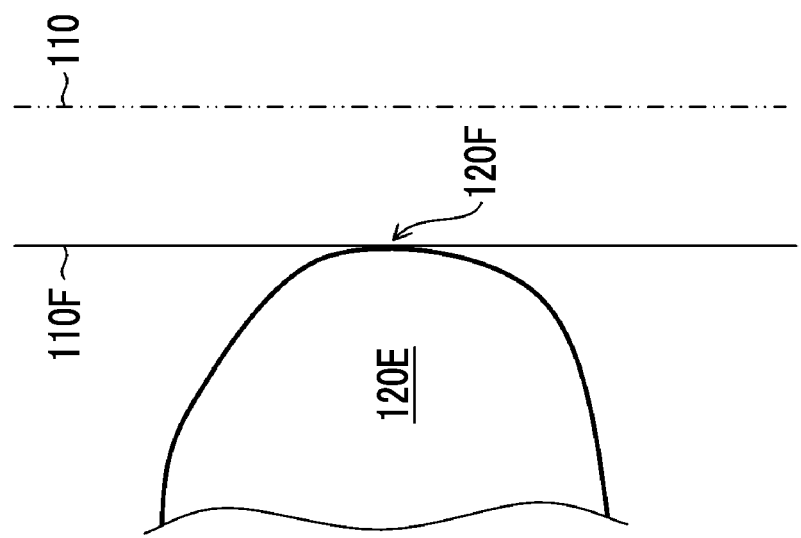
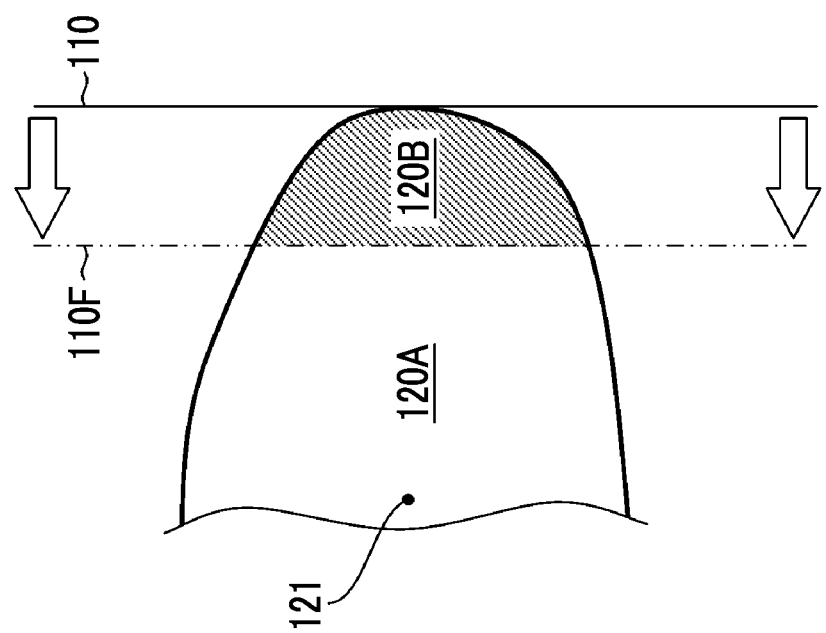

IMAGE PROCESSING APPARATUS, IMAGE PROCESSING METHOD, AND PROGRAM

CROSS-REFERENCE TO RELATED APPLICATIONS

The present application is a Continuation of PCT International Application No. PCT/JP2018/047852 filed on Dec. 26, 2018 claiming priority under 35 U.S.C § 119(a) to Japanese Patent Application No. 2018-012780 filed on Jan. 29, 2018. Each of the above applications is hereby expressly incorporated by reference, in its entirety, into the present application.

BACKGROUND OF THE INVENTION

1. Field of the Invention

The present invention relates to an image processing apparatus, an image processing method, and a program and more particularly, to cooperation between medical image processing and machine learning.

2. Description of the Related Art

In recent years, digitization has progressed in the medical field and a specific region can be automatically extracted from a digital medical image. In addition, it is possible to automatically measure the region extracted from the medical image.

Further, it is possible to perform machine learning using the result of extracting a specific region from a digital medical image and to extract a specific region from the digital medical image using the learning result. Image processing, such as region extraction using deep learning in the medical field, can be performed with high accuracy.

JP2014-502176A discloses an image interpretation system that receives a digital medical image, automatically identifies a measurement element in the image which is related to the calculation of geometrical characteristics in the digital medical image, and automatically calculates the geometric characteristics. The image interpretation system disclosed in JP2014-502176A automatically identifies the center line of the chest, the apex of the heart, the lateral extreme point of the heart, the lateral extreme point of the right lung, and the lateral extreme point of the left lung from the digital chest X-ray to calculate a cardiothoracic ratio.

JP2014-050527A discloses an image processing apparatus that extracts an organ region and a tumor region from a CT image. The image processing apparatus disclosed in JP2014-050527A calculates the displacement of a PET image based on a CT image and deforms the PET image on the basis of the CT image. In addition, CT is an abbreviation of computed tomography. PET is an abbreviation of positron emission tomography.

JP2010-233879A discloses an image measurement device that displays a measurement line on a medical image. The image measurement device disclosed in JP2010-233879A acquires an image file of a medical image and annotation information corresponding to the image file and adds and displays a measurement line and a measurement value on the medical image on the basis of the acquired image file and annotation information. The annotation information is accessory information of the image file related to the measurement line. In a case in which the measurement line is moved, the image measurement device disclosed in JP2010-233879A calculates a measurement value on the basis of the moved measurement line.

JP2008-262253A discloses a curve correction program that, in a case in which a curve is displayed on a display device and any point of the curve is moved, corrects the curve to a curve whose entire trajectory is smoothly continuous, following the movement of the point.

JP2005-224460A discloses a medical image diagnostic apparatus that automatically extracts an organ region in each image from a plurality of images which are spatially or temporally continuous. The medical image diagnostic apparatus disclosed in JP2005-224460A can perform, for example, the movement of a myocardial region, the deformation of the region, the local deletion of the region, and the local addition of the region in a tomographic image of the heart.

JP1992-125779A (JP-H04-125779A) discloses an image processing method that extracts a specific region from a medical image. In the image processing method disclosed in JP1992-125779A (JP-H04-125779A), in a case in which a plurality of images are divided into images inside and outside regions in a plurality of related images, one of the related images is divided into images inside and outside the region and the result of the division is learned. In other related images, regions are automatically extracted using the learning result.

SUMMARY OF THE INVENTION

High-accuracy image processing using machine learning requires high-quality correct answer data. However, it is difficult to collect high-quality correct answer data from the viewpoint of a workload in selecting correct answer images and storing the correct answer images.

JP2014-502176A, JP2014-050527A, JP2010-233879A, JP2008-262253A, and JP2005-224460A disclose techniques related to region extraction, automatic region measurement, and region correction in a medical image and do not disclose the collection of correct answer data used for machine learning.

JP1992-125779A (JP-H04-125779A) discloses a technique for extracting a region of a medical image using machine learning, but does not disclose the collection of correct answer data of machine learning.

The invention has been made in view of the above-mentioned problems and an object of the invention is to provide an image processing apparatus, an image processing method, and a program that can collect high-quality correct answer data used for machine learning with a simple method.

In order to achieve the object, the invention provides the following aspects.

According to a first aspect, there is provided an image processing apparatus comprising: a first extractor that extracts a measurement target region from a medical image, using a result of learning performed using correct answer data of the measurement target region; a measurement object determination unit that determines a measurement object used to measure the measurement target region; a measurement object correction unit that corrects the measurement object in response to a command from a user; and a measurement target region correction unit that corrects the measurement target region extracted by the first extractor, using a correction result of the measurement object. The first extractor performs learning using the measurement target region corrected by the measurement target region correction unit as correct answer data.

According to the first aspect, the correction result of the measurement target region based on the correction result of the measurement object is used as the correct answer data of the first extractor. Therefore, it is possible to collect high-quality correct answer data used for machine learning with a simple method.

The medical image is an image generated from a medical image capture signal. An example of the medical image is a digital X-ray image.

The measurement target region is a region indicating an organ, a bone, a tendon, a muscle, and a tumor included in the medical image and is a target region for calculating a measurement value such as a representative value. The number of measurement target regions may be one or more.

The measurement object is, for example, a line segment, a point, a rectangle, or a symbol for defining the measurement position of the measurement target region.

A set of the measurement target region before correction and the correction result of the measurement target region can be applied as the correct answer data in a case in which the extraction of the measurement target region is learned.

The image processing apparatus according to the first aspect is an image processing apparatus comprising one or more processors and one or more memories. The processor extracts a measurement target region from a medical image, using a result of learning performed using correct answer data of the measurement target region, determines a measurement object used to measure the measurement target region, corrects the measurement object in response to a command from a user, and performs learning, using the corrected measurement target region as correct answer data. The memory may be configured as an image processing apparatus that stores data in each process.

According to a second aspect, in the image processing apparatus according to the first aspect, the measurement target region correction unit may comprise a second extractor that corrects the measurement target region according to the correction of the measurement object, using a result of learning the corrected measurement object and a correction result of the measurement target region corresponding to the correction of the measurement object.

According to the second aspect, it is possible to correct the measurement target region with high accuracy, using the result of learning using the correction result of the measurement target region.

The second extractor can learn the correction of the measurement object, using a set of the correction result of the measurement object and the correction result of the measurement target region as correct answer data.

According to a third aspect, in the image processing apparatus according to the first aspect or the second aspect, the measurement target region correction unit may perform the correction of the measurement target region to change a region which is outside the corrected measurement object in the measurement target region to a non-measurement target region.

According to the third aspect, it is possible to perform correction to delete the measurement target region according to the position of the measurement object.

According to a fourth aspect, in the image processing apparatus according to the first aspect or the second aspect, the measurement target region correction unit may perform the correction of the measurement target region to change a region which is inside the corrected measurement object in a non-measurement target region to the measurement target region.

According to the fourth aspect, it is possible to perform correction to add the measurement target region according to the position of the measurement object.

According to a fifth aspect, in the image processing apparatus according to any one of the first to fourth aspects, the measurement object determination unit may determine a plurality of first line segments parallel to a first direction as the measurement objects and determines a position of one end of the measurement target region and a position of the other end of the measurement target region in a second direction orthogonal to the first direction as positions of the first line segments.

According to the fifth aspect, it is possible to specify the measurement target position of the measurement target region using the measurement object to which the line segment is applied.

According to a sixth aspect, in the image processing apparatus according to the fifth aspect, the measurement target region correction unit may correct a contour of the measurement target region, using a position of the measurement object corrected by the measurement object correction unit as the position of the one end or the position of the other end of the measurement target region in the second direction.

According to the sixth aspect, it is possible to perform the correction of the measurement target region to which a simple process has been applied, without applying a process of designating a large number of points forming the contour of the measurement target region.

According to a seventh aspect, the image processing apparatus according to the fifth aspect or the sixth aspect may further comprise a measurement unit that measures the measurement target region. The first extractor may extract a lung field region and a heart region as the measurement target regions. The measurement object determination unit may determine a position of one end of the lung field region in the second direction, a position of the other end of the lung field region in the second direction, a position of one end of the heart region in the second direction, and a position of the other end of the heart region in the second direction as the positions of the first line segments. The measurement unit may measure a cardiothoracic ratio on the basis of the positions of the plurality of first line segments.

According to the seventh aspect, it is possible to measure the cardiothoracic ratio on the basis of the measurement objects that specify both ends of the lung field region in the second direction and the measurement objects that specify both ends of the heart region in the second direction.

According to an eighth aspect, in the image processing apparatus according to any one of the first to seventh aspects, the first extractor may extract a first measurement target region and a second measurement target region. In a case in which the first measurement target region after correction and the second measurement target region after correction overlap each other, the measurement target region correction unit may correct the second measurement target region according to a correction result of the first measurement target region.

According to the eighth aspect, in a case in which a plurality of measurement target regions are extracted, one measurement target region is corrected according to the correction result of another measurement target region.

According to a ninth aspect, in the image processing apparatus according to any one of the first to seventh aspects, the first extractor may extract a first measurement target region and a second measurement target region. In a case in which the first measurement target region before correction and the second measurement target region before correction come into contact with each other or overlap each other, the measurement target region correction unit may correct the second measurement target region according to a correction result of the first measurement target region.

According to the ninth aspect, in a case in which a plurality of measurement target regions are extracted, it is possible to correct one measurement target region according to the correction result of another measurement target region.

According to a tenth aspect, in the image processing apparatus according to any one of the first to fourth aspects, the measurement object determination unit may determine at least one of a second line segment which connects both ends of the measurement target region in a third direction or a third line segment which connects both ends of the measurement target region in a fourth direction intersecting the third direction as the measurement object.

According to the tenth aspect, it is possible to measure at least one of the overall length of the measurement target region in the third direction and the overall length of the measurement target region in the fourth direction.

According to an eleventh aspect, in the image processing apparatus according to the tenth aspect, the measurement target region correction unit may correct a contour of the measurement target region, using a position of an end of the second line segment corrected by the measurement object correction unit as a position of one end or a position of the other end of the measurement target region in the third direction.

According to the eleventh aspect, it is possible to correct the measurement target region in the third direction according to the correction of the measurement object in the third direction.

According to a twelfth aspect, in the image processing apparatus according to the tenth aspect or the eleventh aspect, the measurement target region correction unit may correct a contour of the measurement target region, using a position of an end of the third line segment corrected by the measurement object correction unit as a position of one end or a position of the other end of the measurement target region in the fourth direction.

According to the twelfth aspect, it is possible to correct the measurement target region in the fourth direction according to the correction of the measurement object in the fourth direction.

According to a thirteenth aspect, in the image processing apparatus according to any one of the tenth to twelfth aspects, the measurement target region correction unit may perform at least one of the correction of the measurement target region to change the measurement target region to the non-measurement target region or the correction of the measurement target region to change the non-measurement target region to the measurement target region, according to at least one of the second line segment after the correction or the third line segment after the correction.

According to the thirteenth aspect, it is possible to replace the measurement target region and the non-measurement target region according to at least one of the second line segment after the correction and the third line segment after the correction.

According to a fourteenth aspect, the image processing apparatus according to any one of the tenth to thirteenth aspects may further comprise a measurement unit that measures the measurement target region. The first extractor may extract a tumor region as the measurement target region and the measurement unit may measure an overall length of the tumor region in the third direction and an overall length of the tumor region in the fourth direction.

According to the fourteenth aspect, it is possible to measure the overall length of the tumor region in the third direction and the overall length of the tumor region in the fourth direction.

According to a fifteenth aspect, in the image processing apparatus according to any one of the first to fourteenth aspects, the measurement target region correction unit may enlarge or reduce the contour of the measurement target region, on the basis of a ratio of a measurement value using the measurement object before correction and a measurement value using the measurement object after correction.

According to the fifteenth aspect, it is possible to correct the measurement target region according to the correction of the measurement object.

According to a sixteenth aspect, the image processing apparatus according to any one of the first to fifteenth aspects may further comprise a signal transmission unit that transmits a signal indicating the measurement object to a display device that displays the medical image.

According to the sixteenth aspect, it is possible to display the measurement object so as to be superimposed on the medical image.

According to a seventeenth aspect, there is provided an image processing method comprising: a first extraction step of extracting a measurement target region from a medical image, using a first extractor that has been trained with correct answer data of the measurement target region; a measurement object determination step of determining a measurement object used to measure the measurement target region; a measurement object correction step of correcting the measurement object in response to a command from a user; a measurement target region correction step of correcting an extraction result of the measurement target region, using a correction result of the measurement object; and a first learning step of training the first extractor, using a correction result of the measurement target region as correct answer data.

According to the seventeenth aspect, it is possible to obtain the same effect as that in the first aspect.

In the seventeenth aspect, the same matters as those specified in the second to sixteenth aspects can be appropriately combined with each other. In this case, the components that are in charge of the processes or functions specified in the image processing apparatus can be understood as components of the image processing method which are in charge of processes or functions corresponding to the processes or functions.

According to an eighteenth aspect, there is provided a program that causes a computer to implement: a first extraction function of extracting a measurement target region from a medical image, using a first extractor that has been trained with correct answer data of the measurement target region; a measurement object determination function of determining a measurement object used to measure the measurement target region; a measurement object correction function of correcting the measurement object in response to a command from a user; a measurement target region correction function of correcting an extraction result of the measurement target region, using a correction result of the measurement object; and a first learning function of training the first extractor, using a correction result of the measurement target region as correct answer data.

According to the eighteenth aspect, it is possible to obtain the same effect as that in the first aspect.

In the eighteenth aspect, the same matters as those specified in the second to sixteenth aspects can be appropriately combined with each other. In this case, the components that are in charge of the processes or functions specified in the image processing apparatus can be understood as components of the program which are in charge of processes or functions corresponding to the processes or functions.

According to the invention, the correction result of the measurement target region based on the correction result of the measurement object is used as the correct answer data of the first extractor. Therefore, it is possible to collect high-quality correct answer data used for machine learning with a simple method.

BRIEF DESCRIPTION OF THE DRAWINGS

FIG. 8 is a diagram schematically illustrating a first example of a deletion process in the correction of a measurement target region.

FIG. 9 is a diagram schematically illustrating a second example of the deletion process in the correction of the measurement target region.

DESCRIPTION OF THE PREFERRED EMBODIMENTS

Figure 1:
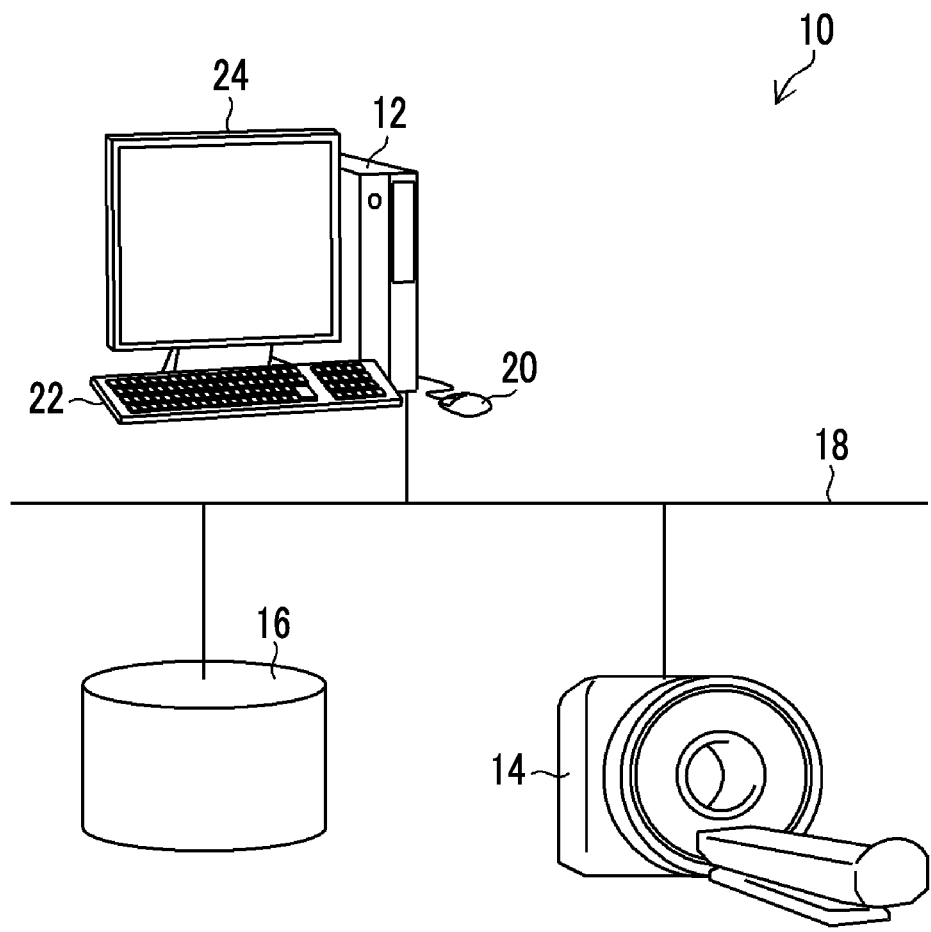
FIG. 1 is a block diagram illustrating an example of the configuration of a medical information system according to an embodiment.

Hereinafter, preferred embodiments of the invention will be described in detail with reference to the accompanying drawings. In the specification, the same components are denoted by the same reference numerals and the description thereof will not be repeated.

[Overall Configuration of Medical Information System]

FIG. 1 is a block diagram illustrating an example of the configuration of a medical information system according to an embodiment. A medical information system 10 comprises an image processing apparatus 12, a modality 14, and an image database 16. The image processing apparatus 12, the modality 14, and the image database 16 are connected through a network 18 so as to communicate with each other. An example of the medical information system 10 is a picture archiving and communication system (PACS).

A computer provided in a medical institution can be applied as the image processing apparatus 12. A mouse 20 and a keyboard 22 as an input device are connected to the image processing apparatus 12. In addition, a display device 24 is connected to the image processing apparatus 12.

The modality 14 is an imaging apparatus that captures an image of an examination target part of a subject and generates a medical image. Examples of the modality include an X-ray imaging apparatus, a CT apparatus, an MRI apparatus, a PET apparatus, an ultrasound apparatus, and a CR apparatus using a flat X-ray detector.

CT is an abbreviation of computed tomography. In addition, MRI is an abbreviation of magnetic resonance imaging. PET is an abbreviation of positron emission tomography. In some cases, a flat X-ray detector is called a flat panel detector (FPD). CR is an abbreviation of computed radiography.

A DICOM standard can be applied as the format of the medical image. Accessory information defined by the DICOM standard may be added to the medical image. DICOM is an abbreviation of digital imaging and communications in medicine.

A computer comprising a high-capacity storage device can be applied as the image database 16. Software for providing the functions of a database management system is incorporated into the computer. In some cases, the database management system is called a database management system (DBMS).

A local area network (LAN) can be applied as the network 18. A wide area network (WAN) may be applied as the network 18. The DICOM standard can be applied as the communication protocol of the network 18. In addition, the network 18 may be configured so as to be connected to a public line network or may be configured so as to be connected to a leased line network.

[Configuration of Image Processing Apparatus]
[Hardware Configuration]

Figure 2:
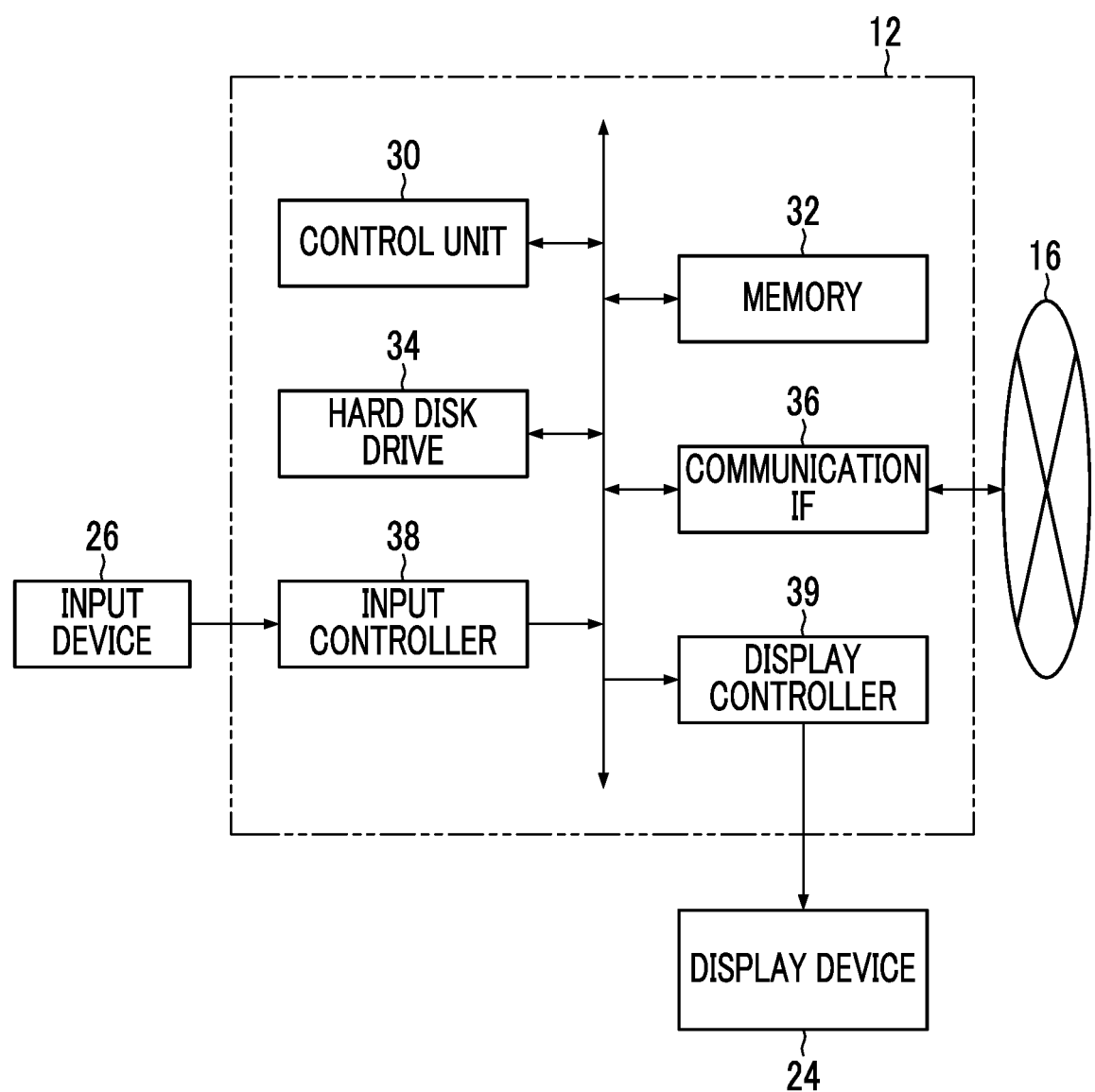
FIG. 2 is a block diagram illustrating an example of the hardware configuration of an image processing apparatus.

FIG. 2 is a block diagram illustrating an example of the hardware configuration of the image processing apparatus. The image processing apparatus 12 comprises a control unit 30, a memory 32, a hard disk drive 34, a communication interface 36, an input controller 38, and a display controller 39.

<Control Unit>

The control unit 30 functions as an overall control unit for the image processing apparatus 12, various arithmetic units, and a storage control unit. The control unit 30 executes programs stored in a read only memory (ROM) provided in the memory 32. The control unit 30 may download a program from an external storage device through the communication interface 36 and may execute the downloaded program. The external storage device may be connected so as to communicate with the image processing apparatus 12 through the network 18.

The control unit 30 performs various processes in cooperation with various programs, using a random access memory (RAM) provided in the memory 32 as an arithmetic region. In this way, various functions of the image processing apparatus 12 are implemented.

The control unit 30 controls the reading of data from the hard disk drive 34 and the writing of data to the hard disk drive 34. The control unit 30 may include one processor or two or more processors.

Examples of the processor include a field programmable gate array (FPGA) and a programmable logic device (PLD). The circuit configuration of the FPGA and the PLD can be changed after the FPGA and the PLD are manufactured.

Another example of the processor is an application specific integrated circuit (ASIC). The ASIC has a dedicated circuit configuration that is designed in order to perform a specific process.

Two or more processors of the same type can be applied as the control unit 30. For example, two or more FPGAs or two PLDs may be used as the control unit 30. Two or more processors of different types may be applied as the control unit 30. For example, one or more FPGAs and one or more ASICs may be applied as the control unit 30.

In a case in which a plurality of control units are provided, the plurality of control units may be configured by one processor. As an example in which the plurality of control units are configured by one processor, a combination of one or more central processing units (CPUs) and software is used to form one processor and the processor functions as the plurality of control units. A graphics processing unit (GPU) which is a processor specialized in image processing may be applied instead of the CPU or in addition to the CPU. Here, the term "software" is synonymous with a program. A computer, such as a client apparatus or a server apparatus, is a representative example in which the plurality of control units are configured by one processor.

As another example in which the plurality of control units are configured by one processor, a processor that implements all of the functions of a system including the plurality of control units with one IC chip is used. A system-on-chip (SoC) is a representative example of the processor that implements all of the functions of the system including the plurality of control units with one IC chip. In addition, IC is an abbreviation of integrated circuit.

As such, the hardware structure of the control unit 30 is configured by one or more various processors.

<Memory>

The memory 32 comprises a ROM (not illustrated) and a RAM (not illustrated). The ROM stores various programs executed by the image processing apparatus 12. The ROM stores, for example, files and parameters used to execute various programs. The RAM functions as a temporary data storage area and a work area of the control unit 30.

<Hard Disk Drive>

The hard disk drive 34 non-transitorily stores various types of data. Specifically, the hard disk drive 34 stores, for example, medical images. The hard disk drive 34 may be attached to the outside of the image processing apparatus 12. A high-capacity semiconductor memory device may be applied instead of or in addition to the hard disk drive 34.

<Communication Interface>

The communication interface 36 performs data communication with external apparatuses such as the modality 14 and the image database 16 illustrated in FIG. 1. IF illustrated in FIG. 2 is an abbreviation of interface.

<Input Controller>

The input controller 38 is an interface that receives a signal transmitted from an input device 26 including the mouse 20 and the keyboard 22 and converts the input signal into a signal in a format that is applied to the image processing apparatus 12.

<Display Controller>

The display controller 39 is an interface that converts a signal indicating the image generated by the image processing apparatus 12 into a video signal displayed by the display device 24. The display controller 39 transmits the video signal indicating the image to the display device 24.

The hardware configuration of the image processing apparatus 12 illustrated in FIG. 2 is illustrative and some components of the hardware configuration can be appropriately added, removed, and changed.

[Functions of Image Processing Apparatus]

Figure 3:
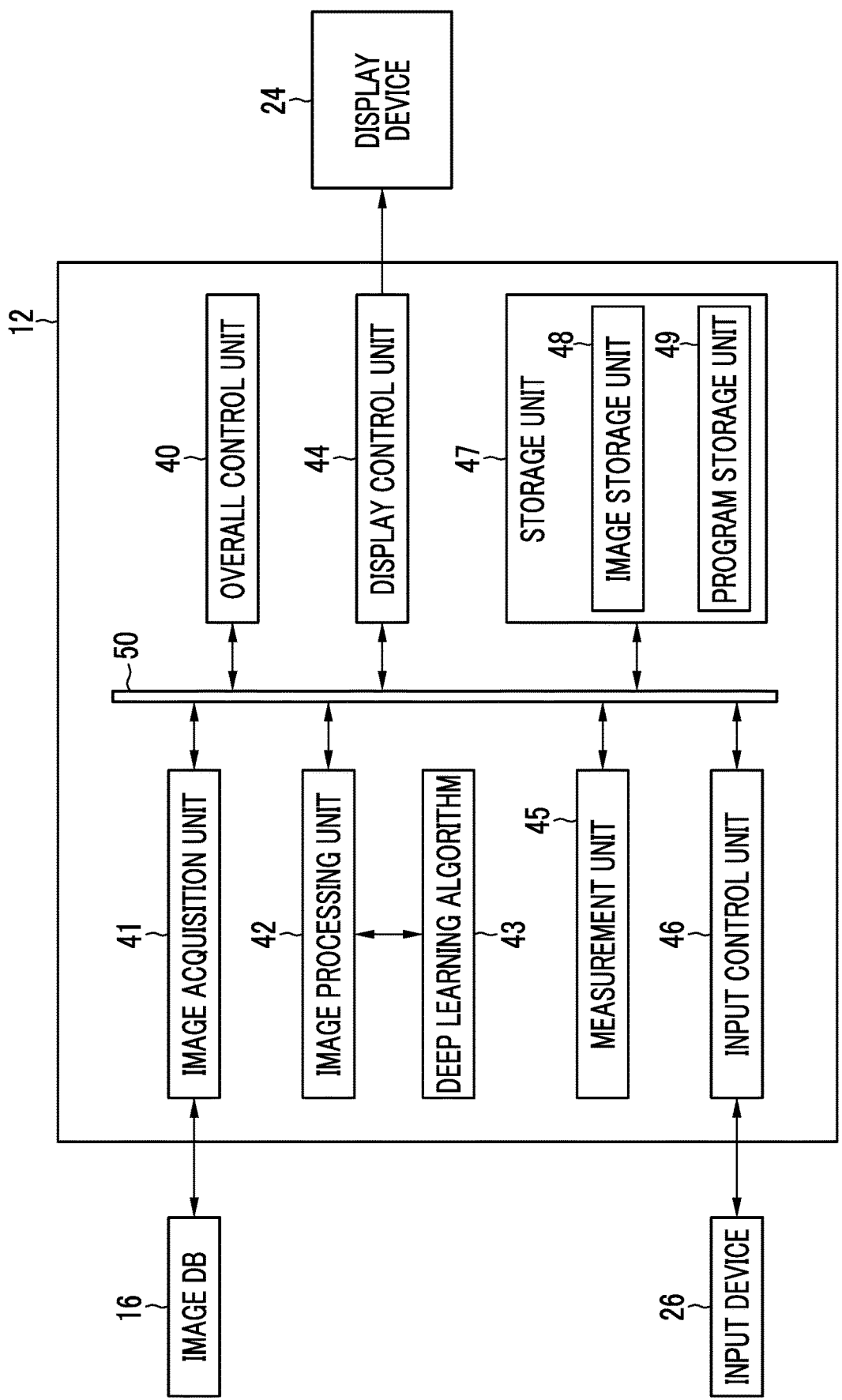
FIG. 3 is a functional block diagram illustrating the functions of the image processing apparatus.

FIG. 3 is a functional block diagram illustrating the functions of the image processing apparatus. The image processing apparatus 12 illustrated in FIG. 3 comprises an overall control unit 40, an image acquisition unit 41, an image processing unit 42, a display control unit 44, a measurement unit 45, an input control unit 46, and a storage unit 47.

The overall control unit 40, the image acquisition unit 41, the image processing unit 42, the display control unit 44, the measurement unit 45, the input control unit 46, and the storage unit 47 are connected through a communication signal line 50 so as to communicate with each other. Hereinafter, each unit will be described in detail.

<Overall Control Unit>

The overall control unit 40 controls the overall operations of the image acquisition unit 41, the image processing unit 42, the display control unit 44, the measurement unit 45, the input control unit 46, and the storage unit 47 on the basis of the execution of a control program of the image processing apparatus 12.

<Image Acquisition Unit>

The image acquisition unit 41 acquires the medical image stored in the image database 16 illustrated in FIG. 1. The image database 16 stores the medical image captured by the modality 14. In this embodiment, a chest X-ray image captured by an X-ray imaging apparatus is exemplified as the medical image.

<Image Processing Unit>

The image processing unit 42 performs an analysis process for the medical image acquired by the image acquisition unit 41, using deep learning based on a deep learning algorithm 43. The analysis process for the medical image will be described in detail below.

The deep learning algorithm 43 is an algorithm including a known convolutional neural network method, a fully connected layer, and an output layer.

The convolutional neural network is a repeated process of a convolution layer and a pooling layer. In some cases, the convolutional neural network is called a convolution neural network. Since the image analysis process using the deep learning is a known technique, the detailed description thereof will not be repeated. In some cases, the convolutional neural network is represented by CNN. CNN is an abbreviation of convolutional neural network.

<Display Control Unit>

In a case in which the medical image is played back by the display device 24, the display control unit 44 functions as a display driver that controls the display of images. The display control unit 44 may display the medical image such that various kinds of information are superimposed on the medical image, using the display device 24.

The display control unit 44 corresponds to an example of a signal transmission unit that transmits a signal indicating a measurement object to a display device displaying a medical image. In addition, the display of the medical image will be described in detail below.

<Measurement Unit>

The measurement unit 45 calculates measurement values, such as a representative value and an analysis value, for a measurement target region, such as an organ, a bone, a tendon, a muscle, or a tumor, included in the medical image. Examples of the measurement value include a cardiothoracic ratio and the overall length of a tumor. The measurement unit 45 calculates the measurement value on the basis of the position of the measurement object that assists measurement. The measurement object and measurement using the measurement object will be described in detail below. The term "measurement value" may be a value that is obtained by statistically processing a plurality of measurement values obtained by performing measurement for the same measurement target a plurality of times. Examples of the statistically processed value include an arithmetic average value and a deviation.

In addition, the measurement unit 45 corrects the measurement value calculated on the basis of the measurement object before correction, on the basis of the correction result of the measurement object. The measurement result and the correction result of the measurement unit 45 are stored in the storage unit 47. The image processing apparatus 12 may display the measurement result and the correction result of the measurement unit 45 using the display device 24.

<Input Control Unit>

The input control unit 46 converts the signal input from the input device 26 into a signal in a format that is applied to the image processing apparatus 12 and transmits the converted signal to the overall control unit 40. The overall control unit 40 controls each unit of the image processing apparatus 12 on the basis of the information input from the input device 26.

<Storage Unit>

The storage unit 47 comprises an image storage unit 48 and a program storage unit 49. The image storage unit 48 stores the medical image acquired by the image acquisition unit 41. The image stored in the image storage unit 48 is read to the image processing unit 42 under the control of the overall control unit 40.

The program storage unit 49 stores various programs for operating the image processing apparatus 12. The various programs stored in the program storage unit 49 are read to each unit under the control of the overall control unit 40.

[Example of Configuration of Image Processing Unit]

Figure 4:
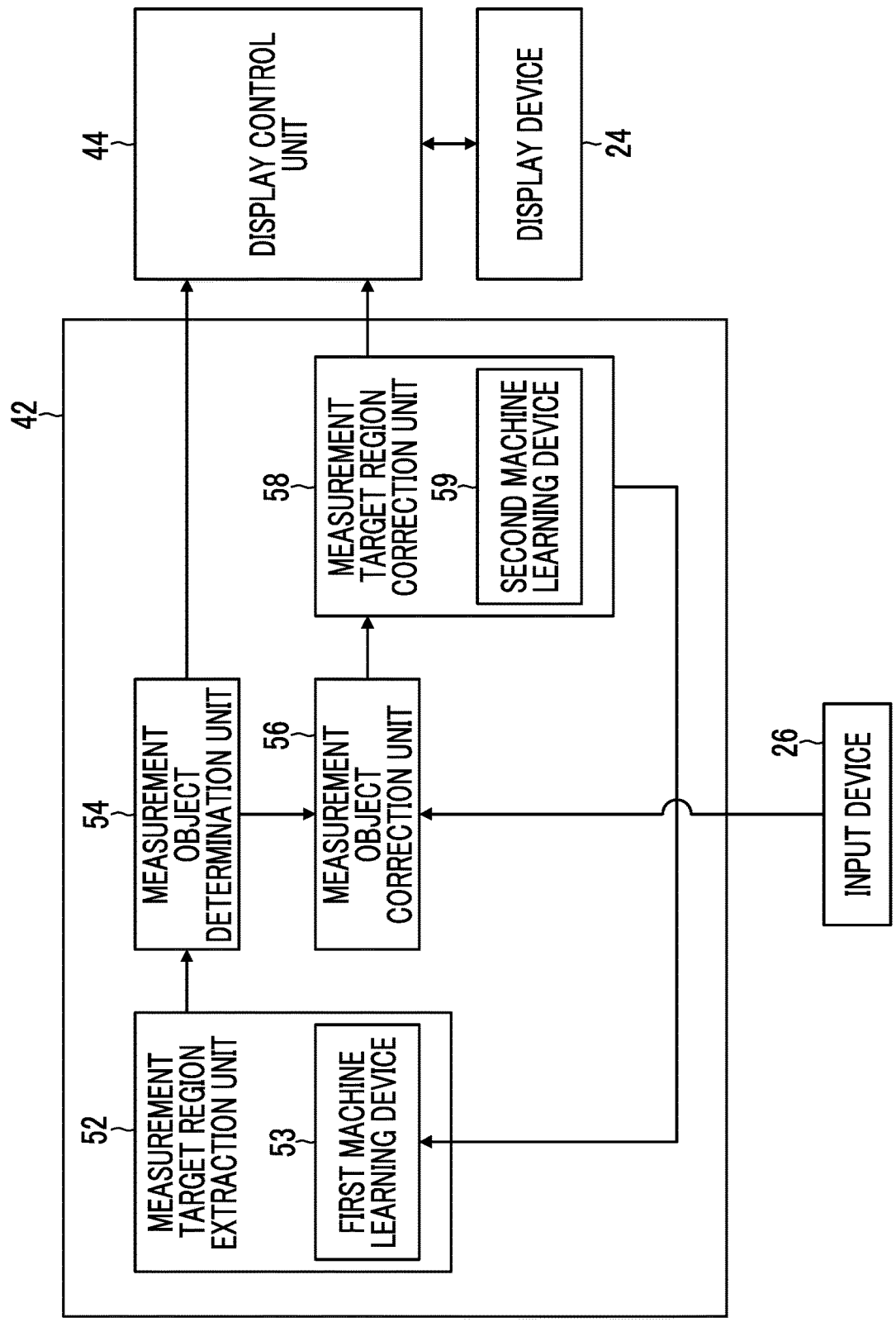
FIG. 4 is a functional block diagram illustrating the functions of the image processing apparatus illustrated in FIG. 3.

FIG. 4 is a functional block diagram illustrating the functions of the image processing unit illustrated in FIG. 3. The image processing unit 42 receives a medical image as an input and automatically extracts, for example, an organ region which is the measurement target region. The image processing unit 42 determines a measurement object for calculating, for example, a representative value and an analysis value on the basis of the extraction result of the measurement target region. The image processing unit 42 has a component for correcting the measurement object and corrects the extraction result of the measurement target region on the basis of the correction result of the measurement object. The image processing unit 42 inputs a set of the measurement target region before correction and the correction result of the measurement target region as correct answer data to an extractor that extracts the measurement target region.

In addition, the image processing unit 42 inputs a set of the correction result of the measurement object and the correction result of the measurement target region as correct answer data to the extractor that corrects the measurement target region. The correct answer data is synonymous with training data in a supervised discriminator.

The measurement object is, for example, a line, a point, or a rectangle for determining the measurement value of the measurement target region of the measurement target used in a case in which the representative value, the analysis value, and the like are calculated. A symbols, such as an arrow, may be used as the measurement object. The measurement object indicates a representative point of the contour line of the measurement target region. In addition, the contour of the measurement target region may be replaced with the outer shape of the measurement target region.

In other words, the image processing unit 42 comprises a component that learns a feature amount related to the measurement target region in advance. A component that segments the measurement target region segments the measurement target region on the basis of the learning result.

The image processing unit 42 comprises a measurement target region extraction unit 52, a measurement object determination unit 54, a measurement object correction unit 56, and a measurement target region correction unit 58. Hereinafter, each unit will be described in detail.

<Measurement Target Region Extraction Unit>

The measurement target region extraction unit 52 extracts a measurement target region from a medical image. For example, the measurement target region extraction unit 52 performs segmentation for the measurement target region from a digital X-ray image which is a medical image.

A first machine learning device 53 is applied to the measurement target region extraction unit 52. That is, the first machine learning device 53 performs learning using the extraction result of the measurement target region as an input. The first machine learning device 53 updates an extraction rule, which is a processing rule of the measurement target region extraction unit 52, using the learning result. The first machine learning device 53 corresponds to an example of a first extractor. The update of the extraction rule is synonymous with the update of an extractor and the update of a machine learning device. In the specification, machine learning may be simply referred to as learning.

<Measurement Object Determination Unit>

The measurement object determination unit 54 determines the position of the measurement object using the extraction result of the measurement target region extraction unit 52. The measurement object determined by the measurement object determination unit 54 is displayed on the display device 24 through the display control unit 44.

<Measurement Object Correction Unit>

The measurement object correction unit 56 corrects the measurement object determined by the measurement object determination unit 54. The measurement object correction unit 56 corrects the measurement object on the basis of measurement object correction information input through the input device 26.

<Measurement Target Region Correction Unit>

The measurement target region correction unit 58 corrects the measurement target region on the basis of the position of the measurement object corrected by the measurement object correction unit 56. The measurement target region correction unit 58 performs the correction of the measurement target region such as the enlargement and reduction of the measurement target region. The measurement target region corrected by the measurement target region correction unit 58 is displayed on the display device 24 through the display control unit 44.

A second machine learning device 59 is applied to the measurement target region correction unit 58. That is, the second machine learning device 59 performs learning using the correction result of the measurement target region as an input. The second machine learning device 59 may perform learning with reference to the anatomical data of the measurement target region. The second machine learning device 59 updates a correction rule which is a processing rule of the measurement target region correction unit 58 using the learning result. The second machine learning device 59 corresponds to an example of a second extractor.

In a case in which the measurement object has been corrected, the display control unit 44 displays the corrected measurement target region based on the corrected measurement object on the display device 24. The components of the image processing unit in the specification can be replaced with components of a medical image analysis processing unit.

[Procedure of Image Processing Method]

Figure 5:
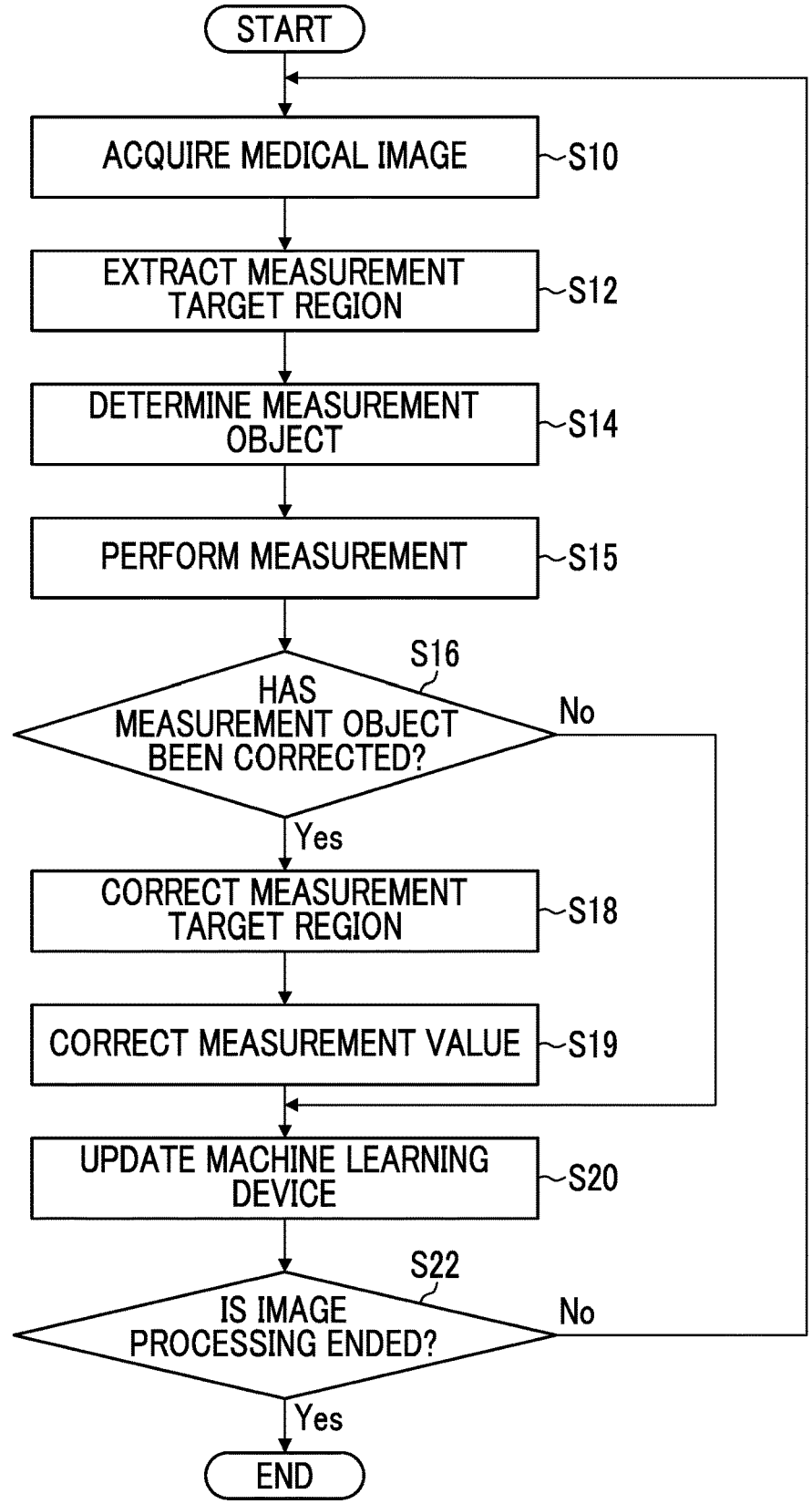
FIG. 5 is a flowchart illustrating the flow of the procedure of an image processing method according to the embodiment.

FIG. 5 is a flowchart illustrating the flow of the procedure of an image processing method according to the embodiment. In a medical image acquisition step S10, the image acquisition unit 41 illustrated in FIG. 3 acquires a medical image. After the medical image is acquired in the medical image acquisition step S10, the process proceeds to a measurement target region extraction step S12.

In the measurement target region extraction step S12, the measurement target region extraction unit 52 illustrated in FIG. 4 extracts a measurement target region from the medical image. After the measurement target region is extracted, the process proceeds to a measurement object determination step S14. The measurement target region extraction step S12 corresponds to an example of a first extraction step.

In the measurement object determination step S14, the measurement object determination unit 54 determines a measurement object. After the measurement object is determined in the measurement object determination step S14, the process proceeds to a measurement step S15.

In the measurement step S15, the measurement unit 45 measures a measurement target region. The measurement result is stored in the storage unit 47. After the measurement value of the measurement target region is calculated in the measurement step S15, the process proceeds to a measurement object correction determination step S16.

In the measurement object correction determination step S16, the measurement object correction unit 56 determines whether or not the measurement object has been corrected. In a case in which the measurement object correction unit 56 determines that the measurement object has not been corrected in the measurement object correction determination step S16, the determination result is "No". In a case in which the determination result is "No", the process proceeds to a machine learning device update step S20.

On the other hand, in a case in which the measurement object correction unit 56 determines that the measurement object has been corrected in the measurement object correction determination step S16, the determination result is "Yes". In a case in which the determination result is "Yes", the process proceeds to a measurement target region correction step S18. The measurement object correction determination step S16 includes a measurement object correction step as a component.

In the measurement target region correction step S18, the measurement target region correction unit 58 corrects the measurement target region on the basis of the correction result of the measurement object. After the measurement target region is corrected in the measurement target region correction step S18, the process proceeds to a measurement value correction step S19.

In the measurement value correction step S19, the measurement unit 45 illustrated in FIG. 3 corrects the measurement value calculated in the measurement step S15 on the basis of the correction result of the measurement object. The corrected measurement value is stored in the storage unit 47 illustrated in FIG. 4. After the measurement value is corrected in the measurement value correction step S19, the process proceeds to a machine learning device update step S20.

In the machine learning device update step S20, the first machine learning device 53 performs machine learning for the extraction of the measurement target region, using a set of the measurement target region before correction and the correction result of the measurement target region as correct answer data. The first machine learning device 53 updates the extraction rule of the measurement target region in the measurement target region extraction step S12 on the basis of the result of the machine learning. After the machine learning device update step S20, the process proceeds to an end determination step S22. The machine learning device update step S20 corresponds to an example of a first learning step.

In the end determination step S22, the image processing unit 42 determines whether or not to end the image processing method. In a case in which the image processing method is continuously performed in the end determination step S22, the determination result is "No". In a case in which the determination result is "No", the process proceeds to the medical image acquisition step S10. Then, the steps from the medical image acquisition step S10 to the end determination step S22 are repeatedly performed until the determination result in the end determination step S22 becomes "Yes".

On the other hand, in a case in which the image processing method is ended in the end determination step S22, the determination result is "Yes". In a case in which the determination result is "Yes", the image processing unit 42 ends the image processing method. The procedure of the image processing method in the specification can be read as the procedure of a medical image analysis process.

[Explanation of Cardiothoracic Ratio Measurement]

<Overall Configuration>

Figure 6:
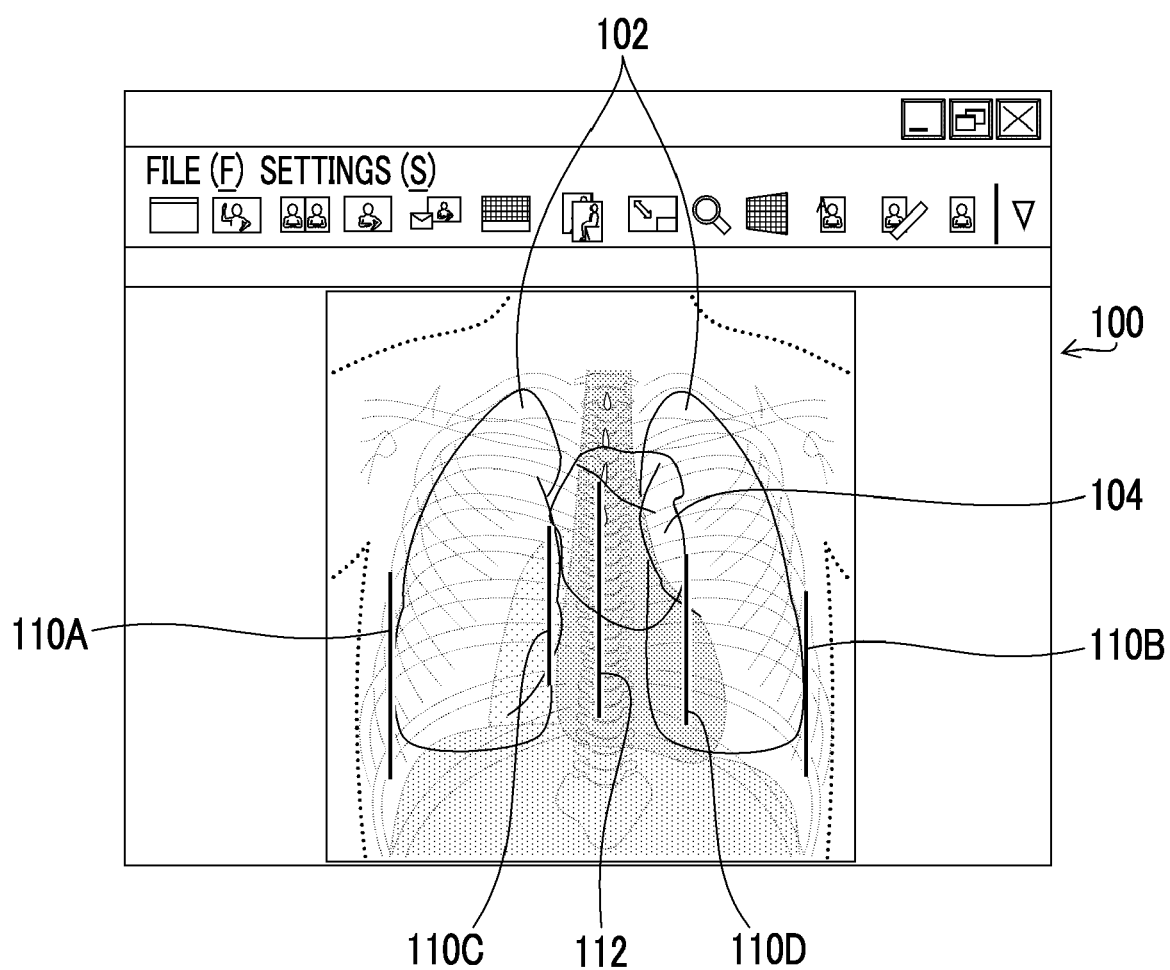
FIG. 6 is a diagram illustrating an example of a screen configuration in the measurement of a cardiothoracic ratio using a chest X-ray image.

Next, cardiothoracic ratio measurement will be described as a specific example of image processing. FIG. 6 is a diagram illustrating an example of a screen configuration in cardiothoracic ratio measurement using a chest X-ray image. In the cardiothoracic ratio measurement, the measurement target region extraction unit 52 illustrated in FIG. 4 automatically extracts a lung field region 102 and automatically extracts a heart region 104 from a chest X-ray image 100.

The measurement object determination unit 54 determines a measurement object 110 on the basis of the extraction results of the lung field region 102 and the heart region 104. In the cardiothoracic ratio measurement, the measurement object determination unit 54 automatically draws parallel line segments which are the measurement objects 110 at the left end of the lung field region 102, the right end of the lung field region 102, the right end of the heart region 104, and the left end of the heart region 104.

That is, the measurement object determination unit 54 determines a first measurement object 110A indicating the left end of the lung field region 102 and a second measurement object 110B indicating the right end of the lung field region 102. Further, the measurement object determination unit 54 determines a third measurement object 110C indicating the left end of the heart region 104 and a fourth measurement object 110D indicating the left end of the heart region 104.

The measurement object 110 is the general term of the first measurement object 110A, the second measurement object 110B, the third measurement object 110C, and the fourth measurement object 110D illustrated in FIG. 6.

The term "parallel" in the specification includes substantially parallel that is strictly non-parallel, but can have the same effect as parallel. The term "orthogonal" in the specification includes substantially orthogonal that is strictly non-orthogonal, but can have the same effect as orthogonal. The term "non-orthogonal" means a case in which the angle formed between two directions is less than 90 degrees or a case in which the angle formed between two directions is greater than 90 degrees.

The image processing unit 42 may display an auxiliary object 112 indicating a median line so as to be superimposed on the chest X-ray image 100. The median line is a line that passes through the center of the entire surface or the back of a living body from the top of the head in the vertical direction. The median line indicates the posture of the subject with respect to the display screen of the chest X-ray image 100.

That is, the image processing unit 42 may comprise an auxiliary object determination unit that determines the auxiliary object 112 indicating the median line. The measurement object determination unit 54 may also be used as the auxiliary object determination unit. The measurement object determination unit 54 may determine the measurement object 110 that is parallel to the median line.

The measurement unit 45 illustrated in FIG. 3 calculates the measurement value of the cardiothoracic ratio using the first measurement object 110A, the second measurement object 110B, the third measurement object 110C, and the fourth measurement object 110D illustrated in FIG. 6.

In a case in which the direction of the measurement object is a first direction and a direction orthogonal to the first direction is a second direction, the cardiothoracic ratio is calculated by multiplying a value, which is obtained by dividing a distance between the third measurement object 110C and the fourth measurement object 110D in the second direction by a distance between the first measurement object 110A and the second measurement object 110B in the second direction, by 100. The unit of the cardiothoracic ratio is percent.

In a case in which it is determined that the measurement object 110 displayed so as to be superimposed on the chest X-ray image 100 is not correctly drawn in the lung field region 102, a doctor who is a user inputs a command to correct the measurement object 110 to a correct position. This holds for a case in which the measurement object 110 is not correctly drawn in the heart region 104.

The first measurement object 110A, the second measurement object 110B, the third measurement object 110C, and the fourth measurement object 110D illustrated in FIG. 6 correspond to examples of a first line segment.

Figure 7:
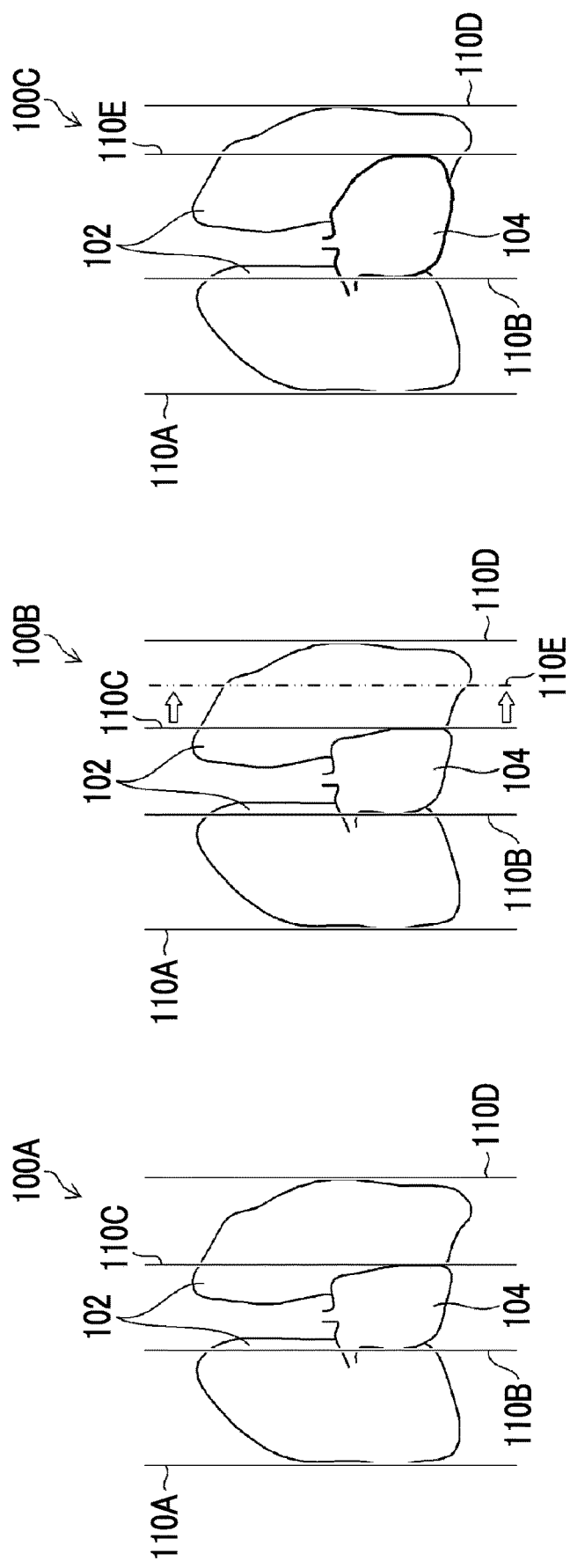
FIG. 7 is a diagram schematically illustrating a measurement target region correction procedure.

FIG. 7 is a diagram schematically illustrating a measurement target region correction procedure. Reference numeral 100A illustrated in FIG. 7 indicates a chest X-ray image on which the measurement object 110 is displayed. Reference numeral 100B illustrated in FIG. 7 indicates a chest X-ray image in a case in which the third measurement object 110C indicating the right end of the heart region 104 has been corrected. The data of a corrected third measurement object 110E is stored in a prescribed storage unit.

In a chest X-ray image 100B, the third measurement object 110C before movement is illustrated using a solid line. Further, in the chest X-ray image 100B, the corrected third measurement object 110E is illustrated using a two-dot chain line.

The movement direction of the measurement object 110 is a direction along a direction orthogonal to the measurement object 110. The corrected third measurement object 110E illustrated in FIG. 7 is parallel to the third measurement object 110C before the movement.

An example of the correction of the measurement object 110 is that any position on the measurement object 110 to be moved is specified by clicking and the measurement object 110 is moved to a movement destination by drag and drop.

Reference numeral 100C illustrated in FIG. 7 indicates a chest X-ray image in which the corrected third measurement object 110E is represented by a solid line. In the chest X-ray image 100C, the heart region 104 has been corrected on the basis of the corrected third measurement object 110E. The heart region 104 illustrated in FIG. 7 has been subjected to an enlargement process, as compared to before the correction.

The measurement unit 45 illustrated in FIG. 3 corrects the measurement value of the cardiothoracic ratio on the basis of the corrected third measurement object 110E. Next, a specific example of the process of correcting the measurement target region will be described in detail.

<Measurement Target Region Deletion Process>

FIG. 8 is a diagram schematically illustrating a first example of a deletion process in the correction of the measurement target region. FIG. 8 schematically illustrates a process of deleting a measurement target region 120A. In the deletion process, in a case in which the measurement object 110 has been corrected, a region which is outside a corrected measurement object 110F in the measurement target region 120A is set as a non-measurement target region 120B. In a case in which the measurement target region 120A is an organ, the non-measurement target region 120B is a non-organ region.

The region outside the corrected measurement object 110F in the measurement target region 120A is the measurement target region 120A that is opposite to a center of gravity 121 of the measurement target region 120A with respect to the corrected measurement object 110F in a case in which the measurement target region 120A and the corrected measurement object 110F intersect each other.

FIG. 8 illustrates the non-measurement target region 120B that is hatched. Reference numeral 120C in FIG. 8 indicates a corrected measurement target region. The contour of the corrected measurement target region 120C has a line segment portion 120D that is parallel to the corrected measurement object 110F and comes into contact with the corrected measurement object 110F.

The measurement target region correction unit 58 may display the corrected measurement target region 120C using the display device 24. The measurement target region correction unit 58 may store the data of the corrected measurement target region 120E without displaying the corrected measurement target region 120C using the display device 24. This holds for a second example, a third example, and the correction of a tumor region which will be described below.

FIG. 9 is a diagram schematically illustrating the second example of the deletion process in the correction of the measurement target region. FIG. 9 schematically illustrates a measurement target region deletion process which, in a case in which the measurement object has been corrected, deletes a region outside the measurement object and adjusts the contour of the measurement target region to an average shape.

In the second example of the deletion process, a known image processing method, such as graph cutting, searching for a density profile, or searching for the most suitable contour, can be applied. This holds for the correction of a tumor region which will be described below.

In the example illustrated in FIG. 9, the corrected measurement target region 120E has a shape that comes into contact with the corrected measurement object 110F at any one point. The contact point of the corrected measurement target region 120E with the corrected measurement object 110F is denoted by reference numeral 120F.

In the deletion process illustrated in FIG. 9, the relationship between the measurement object 110 and the measurement target region is learned in advance and a measurement target region correction rule updated on the basis of the learning result is applied. That is, the second machine learning device 59 illustrated in FIG. 4 performs machine learning for correcting the measurement target region, using a set of the correction result of the measurement object 110 and the correction result of the measurement target region as correct answer data, and updates the measurement target region correction rule applied to the second machine learning device 59.

Figure 10:
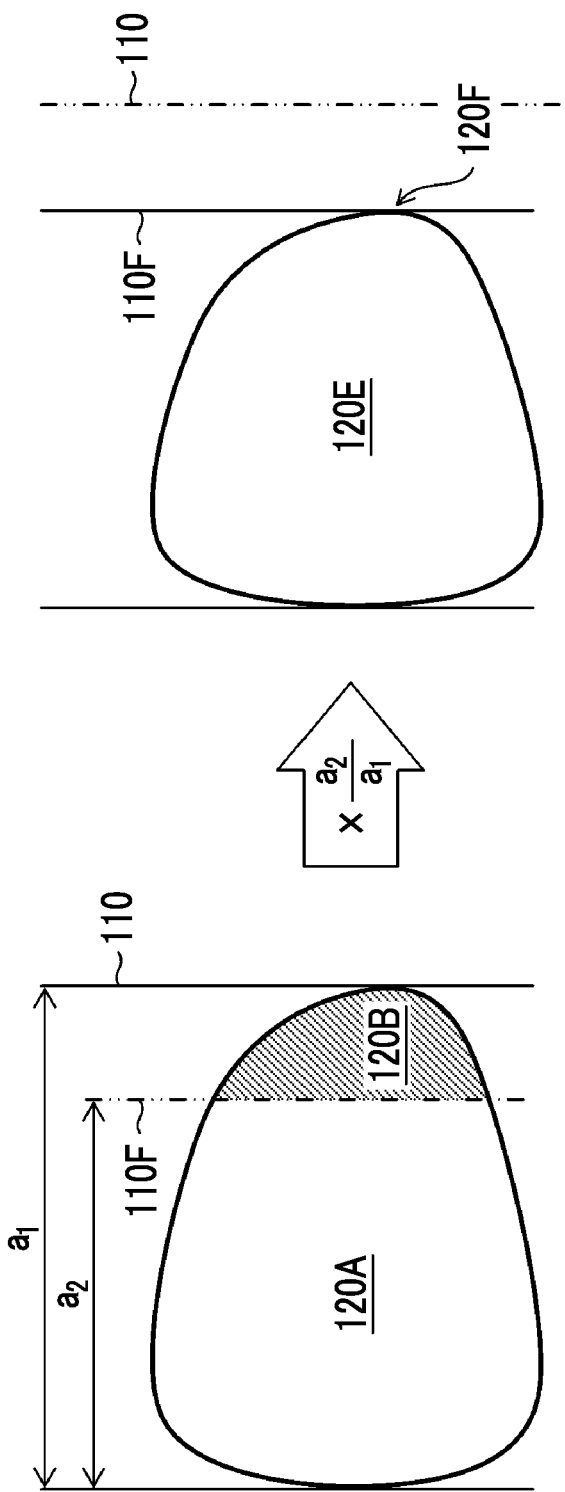
FIG. 10 is a diagram schematically illustrating a third example of the deletion process in the correction of the measurement target region.

FIG. 10 is a diagram schematically illustrating the third example of the deletion process in the correction of the measurement target region. A measurement target region deletion process illustrated in FIG. 10 corrects the contour of the measurement target region according to the ratio of the distances between the measurement objects 110 before and after the movement of the measurement objects 110.

Reference numeral $a_1$ illustrated in FIG. 10 is a distance between the measurement objects 110 before the movement of the measurement objects 110. Reference numeral $a_2$ illustrated in FIG. 10 is a distance between the measurement objects 110 after the measurement objects 110 are corrected. In a case in which the measurement object 110 before correction is corrected to the corrected measurement object 110F, the measurement target region 120A before correction is deformed into the corrected measurement target region 120E, using the ratio $a_2/a_1$.

In addition, the measurement target region extraction unit 52 illustrated in FIG. 4 may perform measurement target region re-extraction as the correction of the measurement target region, using the changed measurement object 110 as a constraint condition. That is, the measurement target region extraction unit 52 and the measurement target region correction unit 58 illustrated in FIG. 4 may be shared, and the first machine learning device 53 and the second machine learning device 59 may be shared.

<Measurement Target Region Enlargement Process>

The above-mentioned measurement target region deletion process can be applied for the measurement target region enlargement process. That is, in the measurement target region enlargement process, the corrected measurement object 110F illustrated in FIG. 9 becomes the measurement object before correction and the measurement object 110 before correction becomes the corrected measurement object.

In addition, the measurement target region enlargement process, the corrected measurement target region 120E becomes the measurement target region before correction, and the measurement target region 120A before correction becomes the corrected measurement target region. This holds for the third example illustrated in FIG. 10.

<Correction Process in Case in which Plurality of Measurement Target Regions are Adjacent to Each Other>

Figure 11:
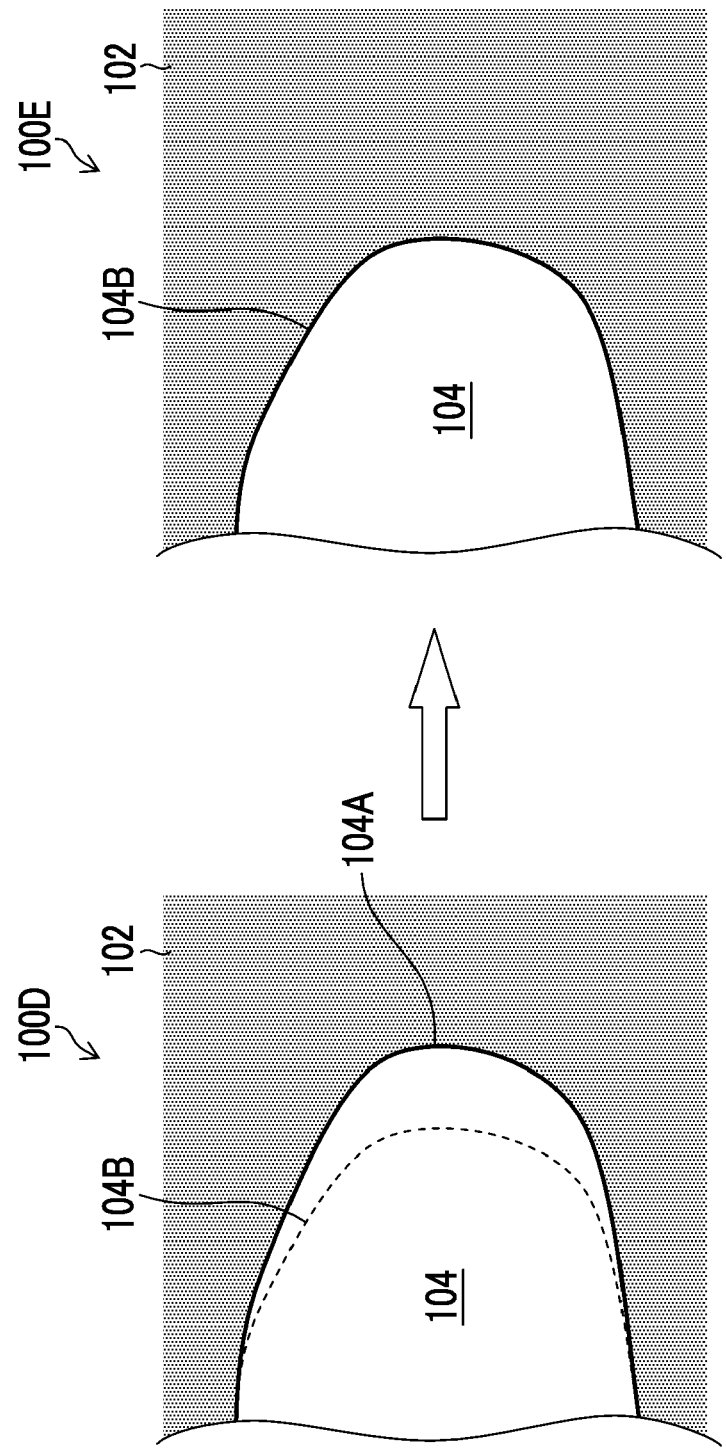
FIG. 11 is a diagram schematically illustrating a correction process in a case in which a plurality of measurement target regions are adjacent to each other.

FIG. 11 is a diagram schematically illustrating a correction process in a case in which a plurality of measurement target regions are adjacent to each other. A chest X-ray image 100D illustrated in FIG. 11 shows a process in a case in which a lung field region 102 and a heart region 104 are adjacent to each other and the heart region 104 is deleted. Reference numeral 104A indicates the contour line of the heart region 104 before correction. Reference numeral 104B indicates the contour line of the heart region 104 after correction.

In a chest X-ray image 100E illustrated in FIG. 11, the deleted heart region 104 is replaced with the lung field region 102. That is, the process of enlarging the lung field region 102 is performed in link with the process of deleting the heart region 104.

In other words, in a case in which the extracted first and second measurement target regions are adjacent to each other, both the first measurement target region and the second measurement target region are corrected at the same time on the basis of one correction process for at least one of the first measurement target region or the second measurement target region.

The second machine learning device 59 illustrated in FIG. 4 learns the relationship between the lung field region 102 and the heart region 104 in advance and applies a correction rule that performs the correction of one of the lung field region 102 and the heart region 104 linked to the correction of the other region based on the learning result. Further, the second machine learning device 59 updates the correction rule using the correction result.

[Explanation of Tumor Measurement]

<Overall Configuration>

Figure 12:
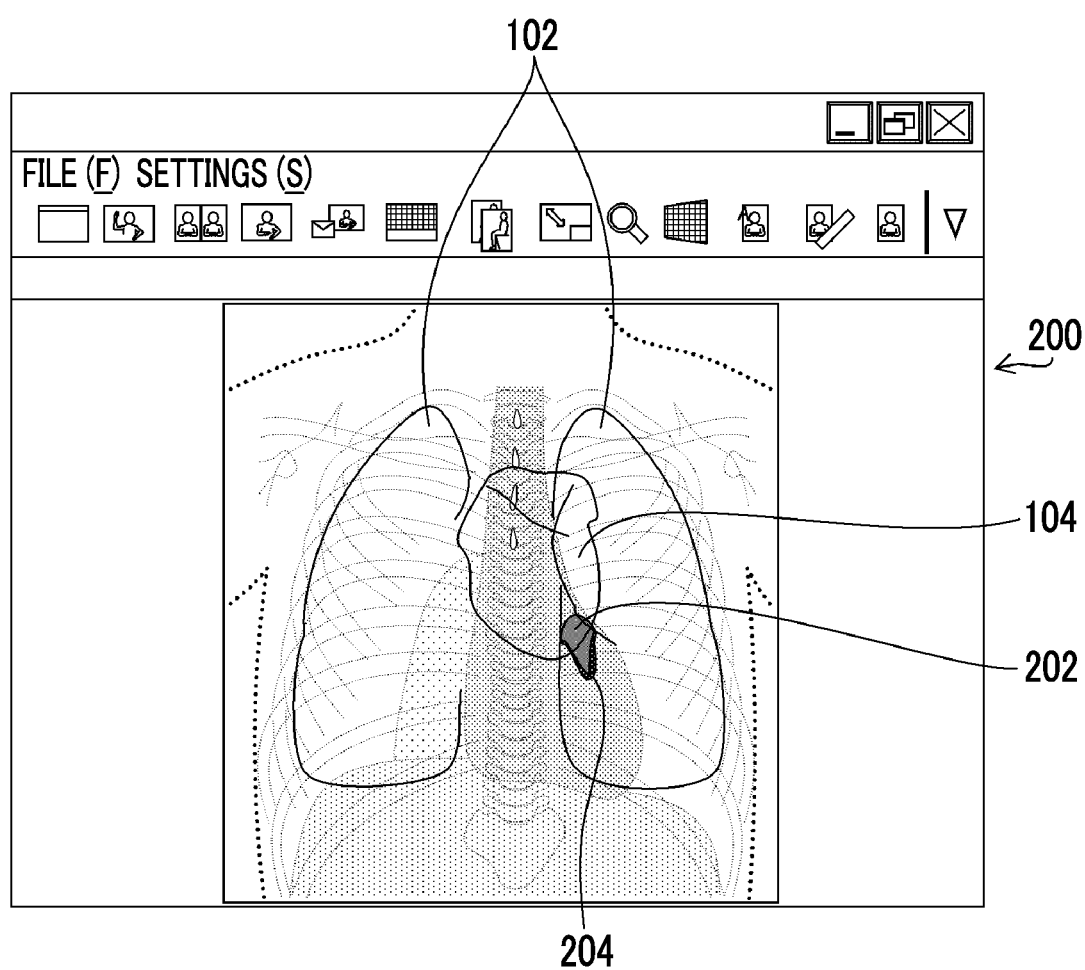
FIG. 12 is a diagram illustrating an example of a screen configuration in tumor measurement using a chest X-ray image.

Next, tumor measurement will be described as another specific example of the image processing. FIG. 12 is a diagram illustrating an example of a screen configuration in tumor measurement using a chest X-ray image. In a chest X-ray image 200 illustrated in FIG. 12, a tumor region 202 is extracted in the lung field region 102.

The measurement target region extraction unit 52 illustrated in FIG. 4 automatically extracts the tumor region 202. FIG. 12 illustrates an example in which the major axis of the tumor region 202 and the minor axis of the tumor region 202 are determined as the measurement objects. Reference numeral 204 illustrated in FIG. 12 denotes a closed curve that indicates the contour of the tumor region 202 and surrounds the tumor region 202. A line segment indicating the major axis of the tumor region 202 is denoted by reference numeral 206 in FIG. 13. A line segment indicating the minor axis of the tumor region 202 is denoted by reference numeral 208 in FIG. 13.

The measurement unit 45 automatically measures the major axis of the tumor region 202 and the minor axis of the tumor region 202. The measurement results of the measurement unit 45 are stored in the storage unit 47. The major axis of the tumor region 202 can be obtained as the maximum value of the length of a line segment that passes through the center of gravity of the tumor region 202 and comes into contact with the contour of the tumor region 202 at two points. The minor axis of the tumor region 202 can be obtained as the minimum value of the length of a line segment that passes through the center of gravity of the tumor region 202 and comes into contact with the contour of the tumor region 202 at two points. The center of gravity of the tumor region 202 is denoted by reference numeral 202A in FIG. 13.

The measurement object determination unit 54 may approximate the tumor region 202 to an ellipse, set the major axis of the ellipse as the major axis of the tumor region 202, and set the minor axis of the ellipse as the minor axis of the tumor region 202. The line segment indicating the major axis of the tumor region 202 and the line segment indicating the minor axis of the tumor region 202 may be superimposed on the chest X-ray image 200, which is not illustrated in FIG. 12.

Figure 13:
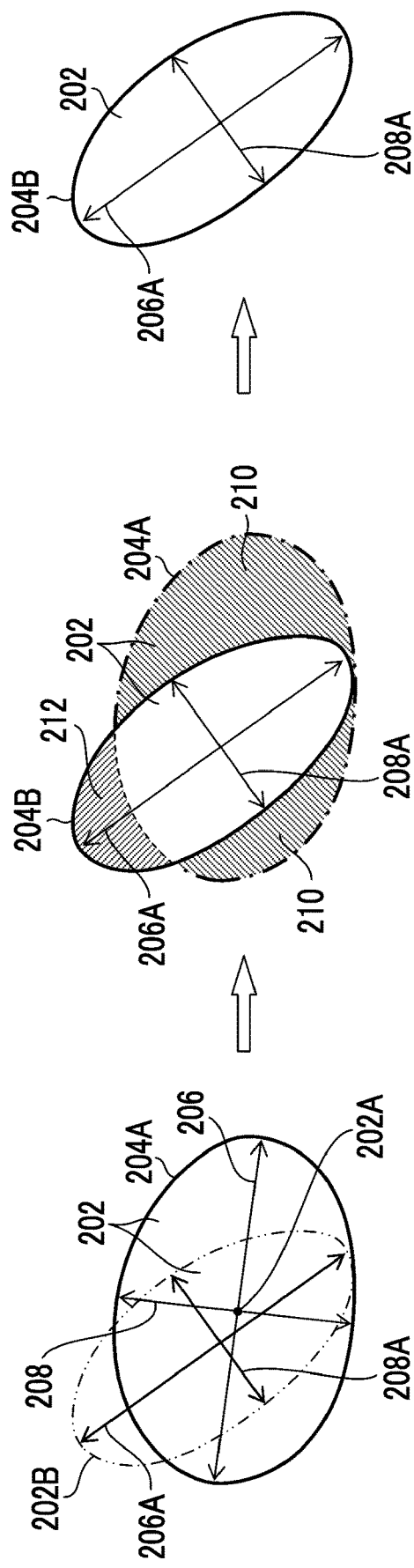
FIG. 13 is a diagram schematically illustrating a region correction process in the tumor measurement.

FIG. 13 illustrates an example in which the tumor region 202 is approximated to an ellipse, the major axis of the tumor region 202 and the minor axis of the tumor region 202 are measured, and the major axis of the tumor region 202 and the minor axis of the tumor region 202 are displayed so as to be superimposed on the chest X-ray image 200 and the contour 204 of the tumor region 202.

In a case in which the doctor determines that the contour 204 of the tumor region 202 displayed so as to be superimposed on the chest X-ray image 200 is not correctly displayed, the doctor accurately corrects at least one of the position of the end of the line segment indicating the major axis of the tumor region 202 or the position of the end of the line segment indicating the minor axis of the tumor region 202. The end of the line segment indicating the major axis of the tumor region 202 represents at least one of both ends of the line segment indicating the major axis of the tumor region 202. This holds for the line segment indicating the minor axis of the tumor region 202.

In a case in which the line segments indicating the major axis of the tumor region 202 and the minor axis of the tumor region 202 have been corrected, the measurement unit 45 re-measures the major axis of the tumor region 202 and the minor axis of the tumor region 202. The re-measurement results of the measurement unit 45 are stored in the storage unit 47. Next, the correction of the measurement target region in the measurement of the tumor region will be described in detail.

<Specific Example of Correction of Region>

FIG. 13 is a diagram schematically illustrating a region correction process in tumor measurement. Reference numeral 204A illustrated in FIG. 13 indicates the contour of the tumor region 202 displayed so as to be superimposed on the chest X-ray image 200. Reference numeral 206 indicates a line segment indicating the major axis of the tumor region 202. Reference numeral 208 denotes a line segment indicating the minor axis of the tumor region 202.

The doctor accurately corrects at least one of the position of the end of the line segment 206 or the position of the end of the line segment 208.

Reference numeral 206A illustrated in FIG. 13 indicates a line segment indicating the major axis of the tumor region 202 after correction. Reference numeral 208A indicates a line segment indicating the minor axis of the tumor region 202 after correction. Reference numeral 204B illustrated in FIG. 13 represents the contour of the tumor region 202 after correction.

That is, the measurement target region correction unit 58 illustrated in FIG. 4 corrects the contour 204A of the tumor region 202 before correction to the contour 204B of the corrected tumor region 202 on the basis of the corrected line segment 206A and the corrected line segment 208A. In this case, the region 210 is deleted from the tumor region 202 before correction and a region 212 is added to the tumor region 202 before correction.

In other words, the measurement target region correction unit 58 sets a region that is outside at least one of the corrected line segment 206A or the corrected line segment 208A in the tumor region 202 before correction as a non-tumor region. In addition, the measurement target region correction unit 58 adds a region that is inside at least one of the corrected line segment 206A or the corrected line segment 208A in the non-tumor region before correction to the corrected tumor region 202.

That is, it is possible to replace the tumor region 202 as the measurement target region and the non-tumor region as the non-measurement target region according to at least one of the corrected line segment 206A or the corrected line segment 208A.

The outside of at least one of the corrected line segment 206A or the corrected line segment 208A indicates the outside of the contour 202B of an ellipse determined by the corrected line segment 206A and the corrected line segment 208A.

The inside of at least one of the corrected line segment 206A or the corrected line segment 208A indicates the inside of the contour of the ellipse determined by the corrected line segment 206A and the corrected line segment 208A.

The outside is a side opposite to the center of gravity of the ellipse with respect to the contour 202B of the ellipse. The inside is a side close to the center of gravity of the ellipse with respect to the contour 202B of the ellipse. The contour 202B of the ellipse is matched with the contour 204B of the corrected tumor region 202.

FIG. 13 illustrates a case in which an elliptical region is created on the basis of the corrected line segment 206A and the corrected line segment 208A as an example of the process of correcting the tumor region 202. The process of correcting the tumor region 202 may generate a polygonal region, such as a quadrangle, on the basis of the corrected line segment 206A and the line segment 208A of the tumor region 202. That is, the extraction of the tumor region 202 may approximate the contour of the tumor region 202 to a circle, an ellipse, or a polygon. This holds for the correction of the tumor region 202.

As another example of the process of correcting the tumor region 202, the relationship among the shape of the tumor region 202, the major axis of the tumor region 202, and the minor axis of the tumor region 202 may be learned by the second machine learning device 59 illustrated in FIG. 4 and the tumor region 202 may be corrected using the learning result.

The direction of the major axis of the tumor region 202 corresponds to an example of a third direction. The direction of the minor axis of the tumor region 202 corresponds to an example of a fourth direction that intersects the third direction. The major axis of the tumor region 202 corresponds to an example of the overall length of the tumor region 202 in the third direction. The minor axis of the tumor region 202 corresponds to an example of the overall length of the tumor region 202 in the fourth direction.

The line segment 206 indicating the major axis of the tumor region 202 corresponds to an example of a second line segment connecting both ends of the tumor region 202 which is the measurement target region in the third direction. The line segment 208 indicating the minor axis of the tumor region 202 corresponds to an example of a third line segment connecting both ends of the tumor region 202 which is the measurement target region in the fourth direction.

The extraction of the tumor region 202 described in this embodiment may be applied to the extraction of a characteristic region such as a tumor or a lesion. Further, the correction of the tumor region 202 may be applied to the correction of a characteristic region such as a tumor and a lesion.

In this embodiment, as the measurement of the tumor region 202, the aspect in which both the major axis of the tumor region 202 and the minor axis of the tumor region 202 are measured has been described. However, at least one of the major axis of the tumor region 202 or the minor axis of the tumor region 202 may be measured in the measurement of the tumor region 202.

[Example of Application to Network System]

Figure 14:
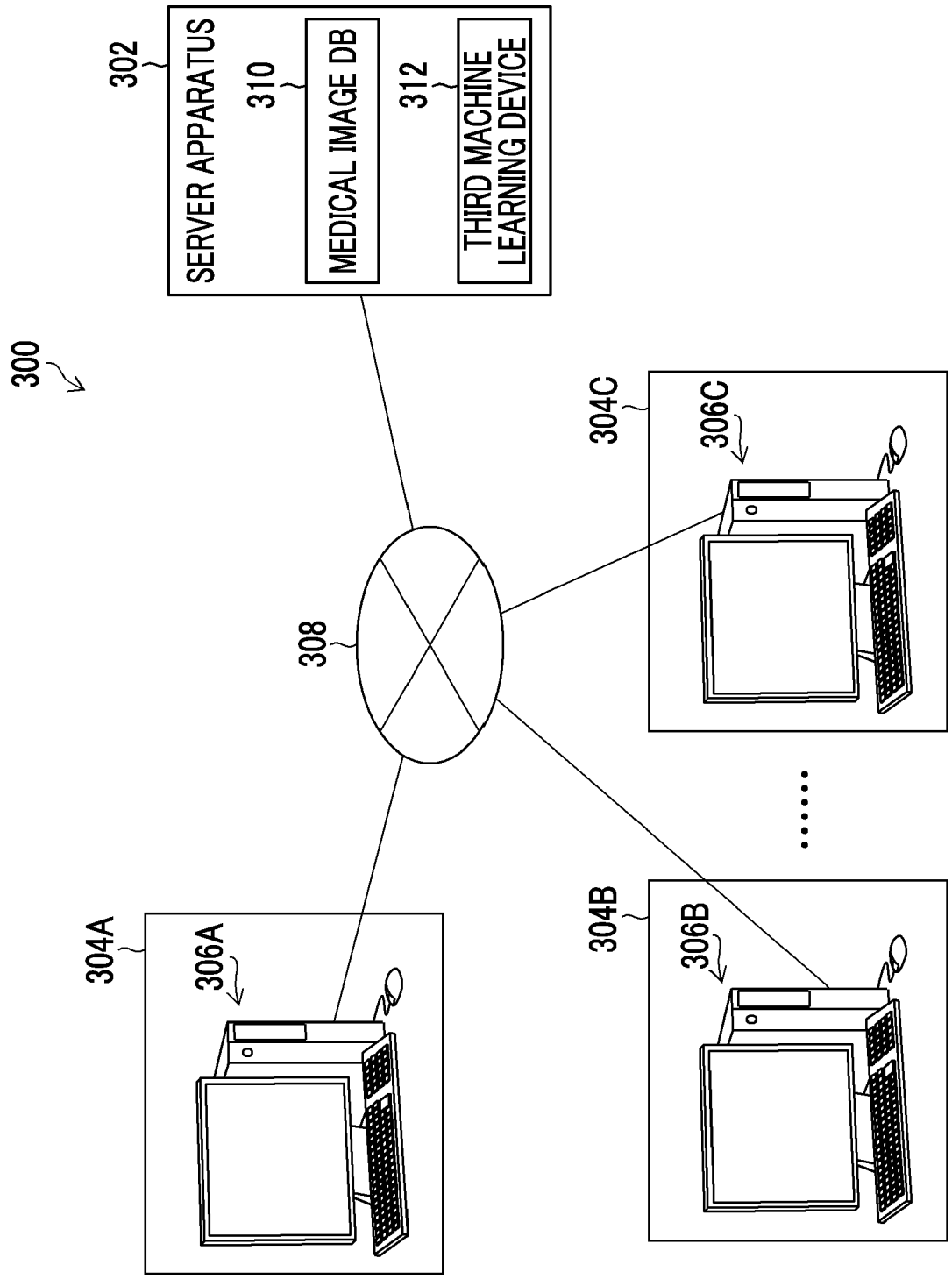
FIG. 14 is a block diagram illustrating an example of the configuration of an information processing system according to the embodiment.

FIG. 14 is a block diagram illustrating an example of the configuration of an information processing system according to the embodiment. An information processing system 300 illustrated in FIG. 14 comprises a server apparatus 302 and a terminal apparatus 306 provided in a medical institution 304. The server apparatus 302 and the terminal apparatus 306 are connected through a network 308 so as to communicate with each other.

The medical institution 304 is a general term of a first medical institution 304A, a second medical institution 304B, and a third medical institution 304C illustrated in FIG. 14. In addition, the terminal apparatus 306 is a general term of a terminal apparatus 306A provided in the first medical institution 304A, a terminal apparatus 306B provided in the second medical institution 304B, and a terminal apparatus 306C provided in the third medical institution 304C illustrated in FIG. 14.

The terminal apparatus 306 has the same configuration and function as the image processing apparatus 12 described with reference to FIGS. 1 to 4. Here, for example, the description of the configuration and function of the terminal apparatus 306 will not be repeated. The terminal apparatus 306 may be connected to the modality provided in the medical institution 304 so as to communicate with the modality. In FIG. 14, the modality is not illustrated. The modality is denoted by reference numeral 14 in FIG. 1.

The server apparatus 302 comprises a medical image database 310 such as the image database 16 illustrated in FIG. 1. The server apparatus 302 is configured such that it can transmit and receive the medical images to and from the terminal apparatus 306 at a high speed. DB illustrated in FIG. 14 is an abbreviation of database.

A network attached storage (NAS) connected to the network 308 can be applied as the medical image database 310. A disk device connected to a storage area network (SAN) can be applied as the medical image database 310.

The server apparatus 302 comprises a third machine learning device 312. A convolutional neural network can be applied as the third machine learning device 312, similarly to the first machine learning device 53 and the second machine learning device 59 illustrated in FIG. 4.

The third machine learning device 312 can have the functions of at least one of the first machine learning device 53 or the second machine learning device 59 illustrated in FIG. 4. The third machine learning device 312 provided in the server apparatus 302 can function as a machine learning device update unit that updates the first machine learning device 53. The third machine learning device 312 can function as a machine learning device update unit that updates the second machine learning device 59.

That is, the third machine learning device 312 may perform machine learning using the extraction result of the measurement target region extraction unit 52 illustrated in FIG. 4 to update the extraction rule applied to the measurement target region extraction unit 52 and to update the first machine learning device 53.

Similarly, the third machine learning device 312 may perform machine learning using the correction result of the measurement target region correction unit 58 illustrated in FIG. 4 to update the correction rule applied to the measurement target region correction unit 58 and to update the second machine learning device 59.

A public line network or a leased line network may be applied as the network 308. A high-speed communication cable, such as an optical fiber, is applied to the network 308. A communication protocol based on the DICOM standard can be applied to the network 308.

[Operation and Effect]

According to the image processing apparatus and the image processing method having the above-mentioned configuration, it is possible to obtain the following operation and effect.

[1]

A measurement target region is extracted from the chest X-ray image 100. The measurement object 110 that assists the measurement of the measurement target region is determined. In a case in which the measurement object 110 is corrected, the measurement target region is corrected on the basis of the correction result of the measurement object 110. The correction result of the measurement target region is fed back to the first machine learning device 53 in association with the correction result of the measurement object 110. This makes it possible to acquire high-quality correct answer data used for machine learning in the extraction of the measurement object using a simple method.

[2]

The measurement target region is extracted, using the result of machine learning using a set of the measurement target region before correction and the correction result of the measurement target region as correct answer data. As a result, it is possible to extract a measurement target region with high accurate.

[3]

The correction result of the measurement target region is fed back to the second machine learning device 59 in association with the correction result of the measurement object 110. This makes it possible to obtain high-quality correct answer data used for machine learning in the correction of the measurement target region using a simple method.

[4]

The measurement target region is corrected, using the result of machine learning using a set of the correction result of the measurement target region and the correction result of the measurement object as correct answer data. Therefore, it is possible to correct the measurement target region with high accuracy according to the correction result of the measurement object.

[5]

A line segment is applied as the measurement object 110. The positions of both ends of the measurement target region in the first direction are determined as the position of the measurement object 110. This makes it possible to specify the measurement target position of the measurement target region, using the measurement object 110 to which the line segment has been applied.

[6]

The measurement target region is corrected using the position of the corrected measurement object 110 as one end of the measurement target region. Therefore, it is possible to perform the correction of the measurement target region to which a simple process has been applied, without applying a process of designating a large number of points forming the contour of the corrected measurement target region.

[7]

A region outside the corrected measurement object 110F in the measurement target region before correction is a non-measurement target region. A region inside the corrected measurement object 110F in the non-measurement target region before correction is set as the measurement target region. Therefore, it is possible to perform at least one of the deletion or the addition of the measurement target region based on the position of the corrected measurement object 110F.

[8]

A line segment along the first direction is applied as the measurement object 110. The positions of both ends of the measurement target region in the second direction orthogonal to the first direction is determined as the position of the measurement object 110. Therefore, it is possible to measure the overall length of the measurement target region in the second direction.

[9]

The measurement target region is corrected such that the corrected measurement object 110F is located at the end of the measurement target region in the second direction. Therefore, it is possible to correct the measurement target region on the basis of the position of the measurement object 110F.

[10]

The positions of both ends of the lung field region 102 in the second direction and the positions of both ends of the heart region 104 in the second direction are determined as the position of the measurement object 110. Therefore, it is possible to measure the cardiothoracic ratio based on the position of the measurement object 110.

[11]

The tumor region 202 is extracted as the measurement target region. At least one of the major axis of the tumor region 202 or the minor axis of the tumor region 202 is determined as the measurement object. Therefore, it is possible to measure at least one of the major axis of the tumor region 202 or the minor axis of the tumor region 202.

[12]

At least one of the major axis of the tumor region 202 or the minor axis of the tumor region 202 is corrected. Therefore, it is possible to correct the tumor region 202.

[13]

In a case in which at least one of the major axis of the corrected tumor region 202 or the minor axis of the corrected tumor region 202 has been corrected, a region which is outside the contour defined by the corrected major axis and the corrected minor axis in the tumor region 202 before the correction is used as the non-measurement target region. A region which is inside the contour defined by the corrected major axis and the corrected minor axis in the non-measurement target region before the correction is used as the measurement target region. Therefore, it is possible to perform at least one of the deletion or the addition of the measurement target region based on the corrected major axis and the corrected minor axis.

[Example of Application to Program Causing Computer to Function as Image Processing Apparatus]

The above-mentioned image processing method can be configured as a program that causes a computer to implement functions corresponding to each step of the image processing method. For example, a program for implementing the following functions may be configured: a first extraction function of extracting a measurement target region from a medical image; a measurement object determination function of determining a measurement object; a measurement object correction function of correcting the measurement object; a measurement target region correction function of correcting the measurement target region using the correction result of the measurement object; and a first learning function of learning the correction result of the measurement target region.

The program causing the computer to implement the image processing functions can be stored in an information storage medium which can be read by the computer and is a non-transitory tangible information storage medium and can be provided through the information storage medium.

In addition, instead of the aspect in which the program is stored in the non-transitory information storage medium and is then provided, a program signal may be provided through the network.

[For Combinations of Embodiments and Modification Examples]

The components described in the above-mentioned embodiments and the components described in the modification examples can be appropriately combined with each other. In addition, some of the components may be replaced.

In the above-described embodiments of the invention, components can be appropriately changed, added, and removed without departing from the scope and spirit of the invention. The invention is not limited to the above-described embodiments and can be changed and modified in various ways by those skilled in the art without departing from the technical idea of the invention.

EXPLANATION OF REFERENCES

10: medical information system
12: image processing apparatus
14: modality
16: image database
18: network
20: mouse
22: keyboard
24: display device
26: input device
30: control unit
32: memory
34: hard disk drive
36: communication interface
38: input controller
39: display controller
40: overall control unit
41: image acquisition unit
42: image processing unit
43: deep learning algorithm
44: display control unit
45: measurement unit
46: input control unit
47: storage unit
48: image storage unit
49: program storage unit
50: communication signal line
52: measurement target region extraction unit
53: first machine learning device
54: measurement object determination unit
56: measurement object correction unit
58: measurement target region correction unit
59: second machine learning device
100: chest X-ray image
100A: chest X-ray image
100B: chest X-ray image
100C: chest X-ray image 100D: chest X-ray image
100E: chest X-ray image
102: lung field region
104: heart region
104A: heart region
110: measurement object
110A: first measurement object
110B: second measurement object
110C: third measurement object
110D: fourth measurement object
110E: corrected third measurement object
110F: corrected measurement object
112: auxiliary object
120A: measurement target region
120B: non-measurement target region
120C: corrected measurement target region
120D: line segment portion
120E: corrected measurement target region
120F: contact point
121: center of gravity
200: chest X-ray image
202: tumor region
204: contour
204A: contour of tumor region before correction
204B: contour of corrected tumor region
206: line segment
206A: line segment after correction
208: line segment
208A: line segment after correction
210: region
212: region
300: information processing system
302: server apparatus
304: medical institution
304A: first medical institution
304B: second medical institution
304C: third medical institution
306: terminal apparatus
306A: terminal apparatus
306B: terminal apparatus
306C: terminal apparatus
308: network
310: medical image database
312: third machine learning device
S10 to S22: each step of image processing method

What is claimed is:

1. An image processing apparatus comprising:
a first extractor that extracts a measurement target region from a medical image, using a result of learning performed using correct answer data of the measurement target region;
a measurement object determination unit that determines a measurement object used to measure the measurement target region;
a measurement object correction unit that corrects the measurement object in response to a command from a user; and
a measurement target region correction unit that corrects the measurement target region extracted by the first extractor, using a correction result of the measurement object,
wherein the first extractor performs learning using the measurement target region corrected by the measurement target region correction unit as correct answer data.

2. The image processing apparatus according to claim 1, wherein the measurement target region correction unit comprises a second extractor that corrects the measurement target region according to the correction of the measurement object, using a result of learning the corrected measurement object and a correction result of the measurement target region corresponding to the correction of the measurement object.

3. The image processing apparatus according to claim 1, wherein the measurement target region correction unit performs the correction of the measurement target region to change a region which is outside the corrected measurement object in the measurement target region to a non-measurement target region.

4. The image processing apparatus according to claim 1, wherein the measurement target region correction unit performs the correction of the measurement target region to change a region which is inside the corrected measurement object in a non-measurement target region to the measurement target region.

5. The image processing apparatus according to claim 1, wherein the measurement object determination unit determines a plurality of first line segments parallel to a first direction as the measurement objects and determines a position of one end of the measurement target region and a position of the other end of the measurement target region in a second direction orthogonal to the first direction as positions of the first line segments.

6. The image processing apparatus according to claim 5, wherein the measurement target region correction unit corrects a contour of the measurement target region, using a position of the measurement object corrected by the measurement object correction unit as the position of the one end or the position of the other end of the measurement target region in the second direction.

7. The image processing apparatus according to claim 5, further comprising:
a measurement unit that measures the measurement target region,
wherein the first extractor extracts a lung field region and a heart region as the measurement target regions,
the measurement object determination unit determines a position of one end of the lung field region in the second direction, a position of the other end of the lung field region in the second direction, a position of one end of the heart region in the second direction, and a position of the other end of the heart region in the second direction as the positions of the first line segments, and
the measurement unit measures a cardiothoracic ratio on the basis of the positions of the plurality of first line segments.

8. The image processing apparatus according to claim 1, wherein the first extractor extracts a first measurement target region and a second measurement target region, and
in a case in which the first measurement target region after correction and the second measurement target region after correction overlap each other, the measurement target region correction unit corrects the second measurement target region according to a correction result of the first measurement target region.

9. The image processing apparatus according to claim 1, wherein the first extractor extracts a first measurement target region and a second measurement target region, and
in a case in which the first measurement target region before correction and the second measurement target region before correction come into contact with each other or overlap each other, the measurement target region correction unit corrects the second measurement target region according to a correction result of the first measurement target region.

10. The image processing apparatus according to claim 1, wherein the measurement object determination unit determines at least one of a second line segment which connects both ends of the measurement target region in a third direction or a third line segment which connects both ends of the measurement target region in a fourth direction intersecting the third direction as the measurement object.

11. The image processing apparatus according to claim 10,
wherein the measurement target region correction unit corrects a contour of the measurement target region, using a position of an end of the second line segment corrected by the measurement object correction unit as a position of one end or a position of the other end of the measurement target region in the third direction.

12. The image processing apparatus according to claim 10,
wherein the measurement target region correction unit corrects a contour of the measurement target region, using a position of an end of the third line segment corrected by the measurement object correction unit as a position of one end or a position of the other end of the measurement target region in the fourth direction.

13. The image processing apparatus according to claim 10,
wherein the measurement target region correction unit performs at least one of the correction of the measurement target region to change the measurement target region to the non-measurement target region or the correction of the measurement target region to change the a non-measurement target region to the measurement target region, according to at least one of the second line segment after correction or the third line segment after correction.

14. The image processing apparatus according to claim 10, further comprising:
a measurement unit that measures the measurement target region,
wherein the first extractor extracts a tumor region as the measurement target region, and
the measurement unit measures an overall length of the tumor region in the third direction and an overall length of the tumor region in the fourth direction.

15. The image processing apparatus according to claim 1,
wherein the measurement target region correction unit enlarges or reduces the a contour of the measurement target region, on the basis of a ratio of a measurement value using the measurement object before correction and a measurement value using the measurement object after correction.

16. The image processing apparatus according to claim 1, further comprising:
a signal transmission unit that transmits a signal indicating the measurement object to a display device that displays the medical image.

17. An image processing method comprising:
a first extraction step of extracting a measurement target region from a medical image, using a first extractor that has been trained with correct answer data of the measurement target region;
a measurement object determination step of determining a measurement object used to measure the measurement target region;
a measurement object correction step of correcting the measurement object in response to a command from a user;
a measurement target region correction step of correcting an extraction result of the measurement target region, using a correction result of the measurement object; and
a first learning step of training the first extractor, using a correction result of the measurement target region as correct answer data.

18. A non-transitory computer readable recording medium which stores commands that, when read by a computer, cause the computer to implement:
a first extraction function of extracting a measurement target region from a medical image, using a first extractor that has been trained with correct answer data of the measurement target region;
a measurement object determination function of determining a measurement object used to measure the measurement target region;
a measurement object correction function of correcting the measurement object in response to a command from a user;
a measurement target region correction function of correcting an extraction result of the measurement target region, using a correction result of the measurement object; and
a first learning function of training the first extractor, using a correction result of the measurement target region as correct answer data.

* * * * *